(12) United States Patent
Baker

(10) Patent No.: US 11,478,524 B1
(45) Date of Patent: Oct. 25, 2022

(54) METHODS AND COMPOSITIONS FOR MODULATING COMPLEX MIXTURES BY SELECTIVE DELETION CHROMATOGRAPHY

(71) Applicant: UNIVERSITY OF SOUTH FLORIDA, Tampa, FL (US)

(72) Inventor: Bill J. Baker, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 985 days.

(21) Appl. No.: 16/050,621

(22) Filed: Jul. 31, 2018

Related U.S. Application Data

(60) Provisional application No. 62/539,391, filed on Jul. 31, 2017.

(51) Int. Cl.
| | |
|---|---|
| *B01D 15/16* | (2006.01) |
| *B01D 15/24* | (2006.01) |
| *B01D 15/32* | (2006.01) |
| *B01D 15/42* | (2006.01) |
| *G01N 30/34* | (2006.01) |
| *G01N 30/72* | (2006.01) |
| *G01N 30/74* | (2006.01) |

(Continued)

(52) U.S. Cl.
CPC ............ *A61K 36/82* (2013.01); *B01D 15/166* (2013.01); *B01D 15/242* (2013.01); *B01D 15/247* (2013.01); *B01D 15/325* (2013.01); *B01D 15/426* (2013.01); *G01N 30/34* (2013.01); *G01N 30/7233* (2013.01); *G01N 30/74* (2013.01);

(Continued)

(58) Field of Classification Search
CPC ............... A61K 36/82; A61K 2236/30; A61K 2236/55; B01D 15/166; B01D 15/242; B01D 15/247; B01D 15/325; B01D 15/426; G01N 30/34; G01N 30/7233; G01N 30/74; G01N 30/8631; G01N 30/8641;

(Continued)

(56) References Cited

U.S. PATENT DOCUMENTS

| | | | | |
|---|---|---|---|---|
| 5,234,586 A | * | 8/1993 | Afeyan | G01N 30/461 |
| | | | | 210/198.2 |
| 2006/0027490 A1 | * | 2/2006 | DeMarco | G01N 30/88 |
| | | | | 210/198.2 |
| 2010/0238444 A1 | * | 9/2010 | Anderson, Jr. | G01N 30/82 |
| | | | | 356/436 |

OTHER PUBLICATIONS

Samanidou, V., "Basic LC Method Development and optimization", Analytical Separation Science, edited by Jared L. Anderson, Alain Berthod, Veronica Pino Estevez, and Apryll M Stalcup. Wiley-VCH Verlag GmbH & Co. KGaA, pp. 25-42 (Year: 2015).*

(Continued)

*Primary Examiner* — Benjamin L Lebron
(74) *Attorney, Agent, or Firm* — Quarles & Brady LLP

(57) ABSTRACT

The present disclosure relates to methods of modifying complex extracts such that components or mixtures of components are selectively removed or added, thus providing a complex mixture that does not naturally occur with a refined or a tuned therapeutic or nutraceutical effect. In various aspects, the complex extract can be an extract obtained from one or more plants, e.g., an extract obtained from green tea leaves. The present disclosure pertains to compositions obtained by the disclosed methods, nutraceutical compositions comprising same, pharmaceutical compositions comprising same, and methods of treating various conditions, including physiological dysfunctions associated with elevated reactive oxygen species and/or inflammatory molecule, e.g., TNFα, expression using same. This abstract is intended as a scanning tool for purposes of searching in the particular art and is not intended to be limiting of the present disclosure.

20 Claims, 4 Drawing Sheets

(51) Int. Cl.
*G01N 30/82* (2006.01)
*G01N 30/86* (2006.01)
*G01N 30/02* (2006.01)
*G01N 30/84* (2006.01)
*A61K 36/82* (2006.01)

(52) U.S. Cl.
CPC ......... *G01N 30/82* (2013.01); *G01N 30/8631* (2013.01); *G01N 30/8641* (2013.01); *A61K 2236/30* (2013.01); *A61K 2236/55* (2013.01); *G01N 2030/027* (2013.01); *G01N 2030/8411* (2013.01)

(58) Field of Classification Search
CPC ..... G01N 2030/027; G01N 2030/8411; G01N 30/80; G01N 30/82
See application file for complete search history.

(56) References Cited

OTHER PUBLICATIONS

Wang, H., and K. Helliwell, "Determination of flavonols in green and black tea leaves and green tea infusions by high-performance liquid chromatography", Food Research International, 34, pp. 223-227. (Year: 2001).*

Bickford et al., Nutraceutical intervention reverses the negative effects of blood from aged rats on stem cells, AGE 37:103,2015.

Martin et al., Synthesis, Stereochemical Analysis, and Derivatization of Myricanol Provide New Probes That Promote Autophagic Tau Clearance, ACS Chem Biol., 10(4): 1099-1109, 2015.

Reygaert, An Update on the Health Benefits of Green Tea, Beverages, 1-14, 2017.

* cited by examiner

METHODS AND COMPOSITIONS FOR MODULATING COMPLEX MIXTURES BY SELECTIVE DELETION CHROMATOGRAPHY

CROSS-REFERENCE TO RELATED APPLICATIONS

This application claims the benefit of U.S. Provisional Application No. 62/539,391, filed on Jul. 31, 2017, which is incorporated herein by reference in its entirety.

BACKGROUND

The academic study of various botanicals for the treatment of diverse diseases has a significant history of biomedical interest. The active principles from many traditional medicines have been extracted from plant sources. Botanicals that have been of interest for their potential therapeutic value include blueberry, bayberry, yarrow, green tea, hollyhock, golden rod, juniper, mandrake and others. The extracts from such plants frequently comprise complex mixtures of alkaloids, glycosides, polyphenols, and terpenes, among others. Plant and other natural extracts have been examined for therapeutic benefit in cardiovascular disease (such as hypertension and hypocholesteremia), infectious disease (such as bacterial and fungal infections), diabetes, and neurodegenerative disorders (see, for example, Bickford et al. 2015; Martin et al. 2015), as well as, health enhancement qualities such as reduction of the risk of cancer and heart disease, protecting brain function, and increasing basal metabolism.

The use of green tea (*Camellia sinensis*) in the last centuries has been accompanied by considerable anecdotal claims of health benefits (Serafini et al. 2011), only recently has the scientific method been brought to bear on both the beverage (infusion product) and chemical extracts of the biological material (capsules, powders) (Khan and Mukhtar 2007; Chacko et al. 2010; Serafini et al. 2011; Yang et al. 2011; Pinto 2013). Such studies include chemical analyses of constituent natural products (Valcic et al. 1996; Sang et al. 2011; van der Hooft et al. 2012), biological screening of extracts and constituent natural products (Braud et al. 2015; Forbes et al. 2015; Suzuki et al. 2016; Szulińska et al. 2017), meta-analyses of screening data (Boehm et al. 2009; Peluso et al. 2013) and most recently, human clinical trials (Yarmolinsky et al. 2015; Molino et al. 2016; Peter et al. 2017). The scope of interest can be judged by the scientific literature which finds a PubMed search returning nearly 7,000 papers in response to 'Green Tea' as an input.

Among health benefits, perhaps the greatest interest in green tea and polyphenols from it has been their antioxidant properties (Yang et al, 2014). Epigallocatechin-3-gallate (EGCG) in particular has well-documented antioxidant activity (Khurana et al, 2013; Nanjo et al, 1999). It can extend lifespan and delay several aging phenotypes under stressful culture conditions (Abbas and Wnk, 2010; Bartholome, et al., 2010; Brown, et al., 2006; Zhang, et al., 2009). This lifespan extension occurs through a DAF-16/FOXO-dependent manner. Interestingly EGCG and quercetin, one of the most abundant natural flavonoids, are selectively concentrated in the mitochondria of mammalian cells (Fiorani, et al., 2010; Schroeder, et al., 2009). EGCG was found to show little effect on longevity under normal conditions, but extended lifespan 13% under heat stress and 178% under oxidative stress (Zhang, et al., 2009). EGCG has been shown to improve the ability of the brain to respond to challenges such as injury or abnormal proteins that accumulate to neurotoxic levels with age (Joseph et al. 1999; Stromberg et al. 2005, Giunta et al., 2010).

Because bioactivity of any extract is a reflection of the activity of individual chemicals in its composition, compounds acting together can increase or decrease effectiveness and potency. Studies of polyphenol interactions with biomolecules (Ozdal et al. 2013; Jakobek 2015) have demonstrated their ability to change, for example, secondary and tertiary structure of proteins (Rawel et al. 2002; Kanakis et al. 2011), protein solubility (Rawel et al. 2002), and to modulate permeability (Pandareesha et al. 2015). Further, the presence of multiple polyphenols in green tea extract means they must compete among themselves for binding sites in a way that purified chemicals do not. While components of green tea have been studied in various combinations, (Dullool et al. 2000; Hsieh and Wu 2009; Tang et al. 2010; Kobalka et al. 2015; Niedzwiecki et al. 2016; Colon et al. 2016), such studies have always started, for good reason, with purified metabolites. However, minor metabolites and complex mixtures of major metabolites are difficult to reconstruct.

Despite the interest and research focused on complex mixtures or extracts from botanicals and other natural sources, there remains a lack accessible methodologies for deconvoluting these mixtures without resorting to laborious purification of individual components and reconstructing the mixtures from purified components. However, even when carried out, such procedures are not amenable to thorough or holistic examination of the complex interactions of the various constituents originally present. In order to rapidly and more completely assess the therapeutic efficacy of complex mixtures, methods are required that can more readily modify such complex and crude mixtures by selectively removing certain components or component mixtures.

There is a need for methods to deconvolute complex interactions within herbal, botanical, or other natural extracts better than reconstructing mixtures from limited pools of purified metabolites. Moreover, there is a need for methods to better understand complex mixtures, e.g., green tea extracts, from a holistic perspective, i.e., the convolution of co-acting or cooperative metabolites (synergistic or additive) with confounding metabolites (antagonistic). Further, there is a need for compositions derived from crude extracts which have been modulated and tuned for particular therapeutic effect by selective removal of certain components or component mixtures. These needs and others are addressed by the present disclosure.

SUMMARY

In accordance with the purpose(s) of the present disclosure, as embodied and broadly described herein, the disclosure, in one aspect, relates to methods of modifying complex extracts such that components or mixtures of components are selectively removed or added, thus providing a complex mixture that does not naturally occur with a refined or a tuned therapeutic or nutraceutical effect. The present disclosure pertains to compositions obtained by the disclosed methods, pharmaceutical compositions comprising same, and methods of treating various conditions, including physiological dysfunctions associated with elevated reactive oxygen species and/or inflammatory molecule, e.g., TNFα, expression using same.

Disclosed are methods of preparing a composition comprising: fractionating an extract sample by liquid chromatography; wherein the extract sample is applied to a liquid chromatography system comprising a chromatography column; and wherein a mobile phase is applied to the chromatography column after the sample is applied to the chromatography column; dividing a total eluant volume into a first eluant stream and a second eluant stream; wherein the first eluant stream comprises a minor fraction by volume of the total eluant volume; and wherein the second eluant stream comprises a majority fraction by volume of the total eluant volume; directing the first eluant stream a detector; wherein the detector is configured to identify components therein; and wherein a detection signal associated with identified components is related to an elution time in the first eluant stream; collecting the second eluant stream; wherein the second eluant stream is collected in a first collected fraction; wherein a portion of the second eluant stream is diverted and collected in a second collected fraction; wherein the portion of the second eluant stream diverted and collected separately corresponds to a component and elution time identified in the first eluant stream by identified by the detector; and wherein after the second collected fraction is obtained, the second eluant stream is returned to collection in the first collected fraction; thereby providing an extract composition with one or more components omitted from the original composition.

Also disclosed are compositions prepared by the disclosed methods. In various aspects, the extract used in the method is prepared from a plant source, e.g., a green tea leaves.

Also disclosed are pharmaceutical compositions comprising a therapeutically effective amount of a disclosed composition and a pharmaceutically acceptable carrier.

Also disclosed are nutraceutical compositions comprising a nutraceutically effective amount of a disclosed composition and a nutraceutically acceptable carrier.

Also disclosed are methods of treating an inflammatory disorder in a mammal comprising the step of administering to the mammal a disclosed composition, a disclosed pharmaceutical composition, or a disclosed nutraceutical composition.

Also disclosed are methods of treating a disease associated with a dysfunction of innate immunity in a mammal comprising the step of administering to the mammal a disclosed composition, a disclosed pharmaceutical composition, or a disclosed nutraceutical composition.

Also disclosed are methods of treating a disease associated with a disease associated with a dysfunction of TNFα expression in a mammal comprising the step of administering to the mammal a disclosed composition, a disclosed pharmaceutical composition, or a disclosed nutraceutical composition.

Also disclosed are kits comprising a disclosed composition, a disclosed pharmaceutical composition, or a disclosed nutraceutical composition; and one or more of: (a) at least one agent known to cause an inflammatory response; (b) at least one agent known to cause a dysfunction in the innate immunity system; (c) at least one agent known to cause a dysfunction in TNFα expression; (d) at least one agent known to treat an inflammatory response; (e) at least one agent known to treat a dysfunction in the innate immunity system; (f) at least one agent known to treat a dysfunction in TNFα expression; (g) instructions for treating an inflammatory response; (h) instructions for treating a dysfunction in the innate immunity system; or (i) instructions for treating to case a dysfunction in TNFα expression.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described aspects are usable in all aspects of the disclosure taught herein. Furthermore, the individual features of the dependent claims, as well as all optional and preferred features and modifications of the described aspects are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A shows the absorbance at 230 nm versus retention time; and FIG. 1B shows the +ESI MS data versus retention time.

Figures 1A, 1B:
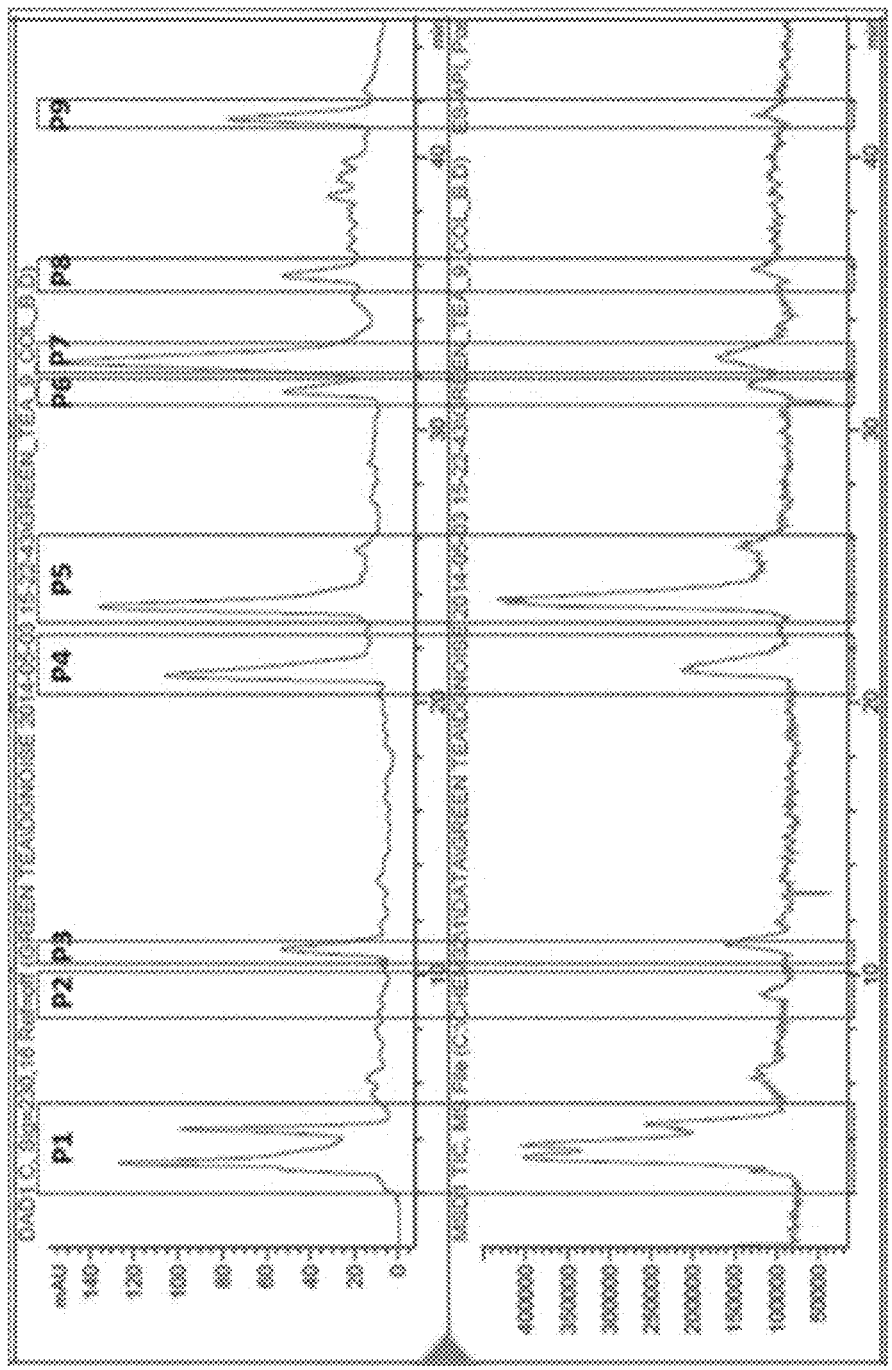
FIGS. 1A and 1B shows a representative mass-directed LC/MS profile obtained using the disclosed methods. The data were obtained using a crude green tea extract obtained from 75 mg green tea and separated on a C18 column (10×250 mm, 5 µm) using a 5 mL/min gradient from 7% aq. MeCN for 10 min, 7%-15% (10-30 min), 15-20% (30-35 min) then 20% (35-44 min).

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The disclosures herein will be described more fully hereinafter with reference to the accompanying drawings, in which some, but not all possible aspects are shown. Indeed, disclosures may be embodied in many different forms and should not be construed as limited to the aspects set forth herein; rather, these aspects are provided so that this disclosure will satisfy applicable legal requirements. Like numbers refer to like elements throughout.

Many modifications and other aspects disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific aspects disclosed and that modifications and other aspects are intended to be included within the scope of the appended claims. Although specific terms are employed herein, they are used in a generic and descriptive sense only and not for purposes of limitation.

It is also to be understood that the terminology used herein is for the purpose of describing particular aspects only and is not intended to be limiting. As used in the specification and in the claims, the term "comprising" can include the aspect of "consisting of." Unless defined otherwise, all technical and scientific terms used herein have the same meaning as commonly understood by one of ordinary skill in the art to which the disclosed compositions and methods belong. In this specification and in the claims which follow, reference will be made to a number of terms which shall be defined herein.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure. Any recited method can be carried out in the order of events recited or in any other order that is logically possible.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided herein can be different from the actual publication dates, which can require independent confirmation.

Prior to describing the various aspects, the following definitions are provided and should be used unless otherwise indicated.

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, "comprising" is to be interpreted as specifying the presence of the stated features, integers, steps, or components as referred to, but does not preclude the presence or addition of one or more features, integers, steps, or components, or groups thereof. Additionally, the term "comprising" is intended to include examples encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a fraction," "a component," or "an injection," including, but not limited to, two or more such fractions, components, or injections, and the like.

Reference to "a" chemical compound refers one or more molecules of the chemical compound, rather than being limited to a single molecule of the chemical compound. Furthermore, the one or more molecules may or may not be identical, so long as they fall under the category of the chemical compound. Thus, for example, "a" polyamide is interpreted to include one or more polymer molecules of the polyamide, where the polymer molecules may or may not be identical (e.g., different molecular weights and/or isomers).

It should be noted that ratios, concentrations, amounts, and other numerical data can be expressed herein in a range format. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'". It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.4%, 3.2%, and 4.4%) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

The terms "treat(s)", "treated", "treating" or "treatment" are used herein interchangeably and refer to any treatment of a disorder in a patient diagnosed or afflicted with such disorder and includes, but is not limited to: (a) caring for a patient diagnosed or afflicted with a disorder; (b) curing or healing a patient diagnosed or afflicted with a disorder; (c) causing regression of a disorder in a patient; (d) arresting further development or progression of a disorder in a patient; (e) slowing the course of a disorder in a patient; (f) relieving, improving, decreasing or stopping the symptoms of a disorder in a patient; (g) relieving, decreasing or stopping the symptoms caused by or associated with a disorder in a patient; or (h) reducing the frequency, number or severity of episodes caused by or associated with a disorder in a patient.

The terms "prevent(s)", "prevented", "preventing" or "prevention" are used herein interchangeably and refer to any prevention or any contribution to the prevention of a disorder in a patient or the development of a disorder if none has occurred in a patient which may be predisposed to such disorder but has not yet been afflicted with or diagnosed as having such disorder.

As used herein, the terms "nutraceutical" and "nutraceutical composition" are broad terms that are used interchangeably and in their ordinary sense to refer to plant-derived products having nutritional or health value.

The term "extract" as used herein, refers to a preparation derived from source material, whether is a plant, microbial, or animal source that is in a different form than the original material from which it is derived. An extract can be as simple as mechanically lysed cells, in which case the preparation may be clarified by centrifugation or filtration to remove insoluble debris, or it can be a preparation derived by contacting the source material with one or more solvents. The term "extract" also encompasses preparations that undergo one or more purification steps to enrich the content of phytochemicals, such as alkaloids, glycosides and/or polysaccharides, as well as preparations comprising partially or substantially purified phytochemicals derived from the plant material.

The term "plant," as used herein, is intended to include both terrestrial and aquatic plants, including various species of seaweed such as, but not limited to, Phaeophyceae, Rhodophyceae or Chlorophyta.

The term "plant material," as used herein, refers to a part or parts of a plant taken either individually or in a group. Examples include, but are not limited to, bulbs, leaves, flowers, fruits, rhizomes, roots, seeds, seed pods, stems, fronds, bark, branchlets, twigs and other parts of a plant.

The term "plant extract," as used herein, refers to a preparation derived from plant material that is in a different form than the original plant material from which it is derived. An extract can be as simple as mechanically lysed cells, in which case the preparation may be clarified by centrifugation or filtration to remove insoluble debris, or it can be a preparation derived by contacting plant material with one or more solvents. The term "extract" also encompasses preparations that undergo one or more purification steps to enrich the content of phytochemicals, such as alkaloids, glycosides and/or polysaccharides, as well as preparations comprising partially or substantially purified phytochemicals derived from the plant material.

The terms "steroid" and "steroid-like" are used interchangeable herein and refer to a general class of polycyclic compounds possessing the skeleton of cyclopentanophenanthrene or a skeleton derived there from by one or more bond scissions or ring expansions or contractions. The rings may be substituted at one or more positions, to create derivatives that adhere to the rules of valence and stability, such as by methyl or other lower alkyl groups, hydroxyl groups, alkoxyl groups and the like.

The term "reactive oxygen species" or "ROS", as used herein, means molecular compounds or ionic compounds or molecular structures or ionic structures or molecular compounds and ionic compounds and molecular structures and ionic structures characterized by the inclusion of a partially reduced oxygen atom or an oxygen atom susceptible to partial reduction or a partially reduced oxygen atom and an oxygen atom susceptible to partial reduction including but not limited to; singlet oxygen or superoxide or hydroperoxyl or peroxide or hydroxyl radical or hypochlorous acid or peroxynitrite or nitrogen dioxide or nitrosoperoxycarbonate or dinitrogen trioxide or singlet oxygen and superoxide and hydroperoxyl and peroxide and hydroxyl radical and hypochlorous acid and peroxynitrite and nitrogen dioxide and nitrosoperoxycarbonate and dinitrogen trioxide. In various aspects, disclosed compositions modulate the levels of ROS in a cell or organism. In a further aspect, disclosed compositions modulate the levels of ROS in a cell or organism, e.g., after exposure of the cell or organism to a pro-inflammatory agent or molecule.

As used herein, "TNF modifying composition" or "TNFα modifying composition" means an composition that affects an intracellular or extracellular molecule or agent associated with the TNFα inflammatory cascade. For example, an intracellular molecule can be a molecule associated with signal transduction in the TNF inflammatory cascade and includes small molecule chemical agents and biological agents, such as polynucleotides and polypeptides, which include antibodies and fragments thereof, antisense, small interfering RNA (siRNA), and ribozymes. Alternatively, an agent can act extracellularly via modifying the action of TNFα at a TNFα cell surface receptor and agents that affect the action of secreted molecules associated with the TNF inflammatory cascade, such as IL-1, IL-6, and HMG-B1. Extracellular TNFα modifying agents include small molecule chemical agents and biological agents, such as polynucleotides and polypeptides, which include antibodies and fragments thereof, antisense, small interfering RNA (siRNA), and ribozymes. In various aspects, disclosed compositions are TNFα modifying compositions.

As used herein, "TNF blocking composition" or "TNFα blocking composition" means any composition or agent that has an inhibitory effect on TNFα, its intracellular inflammatory cascade, and its associated secreted agents and includes a composition that exerts its effect either intracellularly and extracellularly TNFα modifying agents. In various aspects, disclosed compositions are TNFα blocking compositions.

As used herein, the terms "optional" or "optionally" means that the subsequently described event or circumstance can or cannot occur, and that the description includes instances where said event or circumstance occurs and instances where it does not.

The term "subject," as used herein, refers to a mammal in need of treatment or who would otherwise benefit from the use of the system of the disclosure.

Unless otherwise specified, temperatures referred to herein are based on atmospheric pressure (i.e. one atmosphere).

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

Selective Deletion Chromatography

In various aspects, the present disclosure pertains to methods of preparing a composition comprising use of selective deletion chromatography as disclosed herein. In an aspect, the methods for selective deletion chromatography can be used to prepare a composition for use in a pharmaceutical composition as disclosed herein. In a further aspect, the methods for selective deletion chromatography can be used to prepare a composition for use in a nutraceutical composition as disclosed herein.

In various aspects, the disclosed selective deletion chromatography methods comprise fractionating a complex mixture, e.g., a crude extract of a natural source material such as a crude extract of a plant material, by preparative mass-directed liquid chromatography/mass spectrometry (LC/MS), wherein a small portion of the LC output can be diverted to a mass spectrometer while the majority of the sample flows to a fraction collector. Controller software can be used to deconvolute mass spectroscopic data to identify compounds by their major ion (base peak). Individual deconvoluted components of the mixture are captured in their own collection vessels with concomitant retention and mass data. The remainder of the output from the HPLC can be collected in a single vessel. The method can further comprise removal of the solvent(s) of the mobile phase used in the chromatography. Accordingly, the composition thus prepared will constitute the original extract sans selected component(s). The new mixture, minus the selected component, is referred to herein as a subtracted mixture. Accordingly, in various aspects, the disclosed selective deletion chromatography methods are useful optimizing crude extracts, e.g., herbal extracts such as extracts from green tea leaves, for specific indications or uses.

As used herein, an "edited mixture" refers to a crude mixture which has been subject to removal of one or more peaks identified in the crude mixture using the disclosed selective deletion chromatography methods. As disclosed herein below in the Examples, it was determined that fundamental differences in the original, untreated, mixture compared not only to the individual components separated from the mixture, but from the subtracted mixture as well. This 'edited mixture prepared by the disclosed selective deletion chromatography methods can provide mixtures that allow one to characterize and understand the physical, chemical and biological properties of one or more components of an mixture from that observed in the overall mixture. The method does not require a priori knowledge of the structure or chemical composition of a peak that is removed. However, once an effect on a biological activity is observed for removing one or more components from a complex mixture, the method can further comprise structural chemical identification of the component(s) in the removed fraction.

In various aspects, the method can further comprise enriching a crude mixture with one or more fractions isolated by selective deletion chromatography.

In various aspects, the method can further comprise enriching an edited mixture prepared as described with one or more fractions isolated by selective deletion chromatography.

In various aspects, various combinations of subtraction and addition workflows can be combined to generate a wide variety of specifically edited and added compositions. In a further aspects, the various combinations of subtraction and addition workflows can be utilized for different plant extracts, and the resulting plant extract edited composition can be combined with one or more plant extract edited compositions obtained from different plant types.

In a further aspect, the methods for selective deletion chromatography can be used to prepare an edited composition for use as a research tool as disclosed herein. For example, selective deletion chromatography can be used to prepare an extract with one or more components removed from the extract such that the multiple roles, positive and negative, of individual components and component mixtures have on observed bioactivity can be readily determined. As disclosed herein, an exemplary extract, i.e., an extract prepared from green tea leaves, was subjected to the disclosed selective deletion chromatography and the resulting edited extracts were assessed using assays of activation of the innate immune system and ROS production, and it was determined that a whole crude extract can be modulated for specific enhanced or decreased activities based on the selective deletion chromatography of specific component materials, e.g., metabolites, found in the crude extract. Accordingly, in various aspects, the disclosed selective deletion chromatography methods can be used to determine optimal configurations of extracts prepared from natural sources to identify compositions that cannot be found in nature per se.

In an aspect, the present disclosure pertains to methods of preparing a composition comprising: fractionating an extract sample by liquid chromatography; wherein the extract sample is applied to a liquid chromatography system comprising a chromatography column; and wherein a mobile phase is applied to the chromatography column after the sample is applied to the chromatography column; dividing a total eluant volume into a first eluant stream and a second eluant stream; wherein the first eluant stream comprises a minor fraction by volume of the total eluant volume; and wherein the second eluant stream comprises a majority fraction by volume of the total eluant volume; directing the first eluant stream a detector; wherein the detector is configured to identify components therein; and wherein a detection signal associated with identified components is related to an elution time in the first eluant stream; collecting the second eluant stream; wherein the second eluant stream is collected in a first collected fraction; wherein a portion of the second eluant stream is diverted and collected in a second collected fraction; wherein the portion of the second eluant stream diverted and collected separately corresponds to a component and elution time identified in the first eluant stream by identified by the detector; and wherein after the second collected fraction is obtained, the second eluant stream is returned to collection in the first collected fraction; thereby providing an extract composition with one or more components omitted from the original composition.

Green Tea Compositions

In various aspects, as described herein below, an exemplary aspect of the disclosed selective deletion chromatography methods comprises injecting a green tea extract sample onto an Agilent preparative 1200 LC/6120B single-quad mass spectrometer that was programmed to divert fractions based on detector response (i.e., an eluting peak). An exemplary chromatographic profile is shown in FIG. 1A (detection by UV spectrometry at 230 nm) and 1B (detection by mass spectrometry, +ESI MS). In this example, FIG. 1A identifies a number of peaks labeled P1-P9. In an aspect, separation of a complex mixture, a green tea extract, can be conducted where fraction P1 is diverted to one collection vessel, everything else to a separate vessel. The two resultant collected samples then are P1, which is a mixture of two closely eluting peaks shown in FIG. 1A, and a 'extract minus P1 (E-P1)' sample. In a further aspect, a composition can be prepared wherein the peak corresponding to P2 is diverted to one vessel, the remainder to a separate one, resulting in P2 and E-P2 samples. Thus, in various aspects, compositions can be prepared in which each of the labeled peaks (P1-P9) are subtracted from the original crude mixture. In a further aspect, one or more such peaks can be subtracted from the original crude mixture.

In an aspect, the method can further comprise enriching a crude green tea mixture with one or more fractions isolated by selective deletion chromatography. For example, using the green tea extract described in FIG. 1A to illustrate, the method can comprise accumulation of fractions such as one or more of P1-P9, and then selectively adding purified fractions back to the original crude mixture. The addition-edited mixtures can provide a further tool to both understanding and characterizing a crude mixture, as well as fine tuning or optimizing a crude mixture for desired bioactive properties.

In various aspects, the method can further comprise enriching an edited mixture prepared as described with one or more fractions isolated by selective deletion chromatography. For example, a green tea extract as described in FIG. 1A, the method can comprise accumulation of fractions such as one or more of P1-P9, and then selectively adding purified fractions back to an edited mixture. In a particular example, an edited mixture in which P2 has been removed by the disclosed methods and be further supplement with an isolated P1 and/or P3-P9 fraction. The addition-edited mixtures can provide a further tool to both understanding and characterizing a crude mixture, as well as fine tuning or optimizing a crude mixture for desired bioactive properties.

In various aspects, various combinations of subtraction and addition workflows can be combined to generate a wide variety of specifically edited and added compositions obtained from green tea extracts. In a further aspects, the various combinations of subtraction and addition workflows for green tea extracts can be utilized with different plant extracts, i.e., an edited green tea extract can be combined with one or more edited compositions obtained from one or more extracts that is not a green tea extract.

In a further aspect, the methods for selective deletion chromatography can be used to prepare an edited green tea composition for use as a research tool as disclosed herein. For example, selective deletion chromatography can be used to prepare an extract with one or more components removed from the extract such that the multiple roles, positive and negative, of individual components and component mixtures have on observed bioactivity can be readily determined. As disclosed herein, an exemplary extract, i.e., an extract prepared from green tea leaves, was subjected to the disclosed selective deletion chromatography and the resulting edited extracts were assessed using assays of activation of the innate immune system and ROS production, and it was determined that a whole crude extract can be modulated for specific enhanced or decreased activities based on the selective deletion chromatography of specific component materials, e.g., metabolites, found in the crude extract. Accordingly, in various aspects, the disclosed selective deletion chromatography methods can be used to determine optimal configurations of extracts prepared from natural sources to identify compositions that cannot be found in nature per se.

In an aspect, the present disclosure pertains to methods of preparing a composition comprising: fractionating a green tea extract sample by liquid chromatography; wherein the green tea extract sample is applied to a liquid chromatography system comprising a chromatography column; and wherein a mobile phase is applied to the chromatography column after the sample is applied to the chromatography column; dividing a total eluant volume into a first eluant stream and a second eluant stream; wherein the first eluant stream comprises a minor fraction by volume of the total eluant volume; and wherein the second eluant stream comprises a majority fraction by volume of the total eluant volume; directing the first eluant stream a detector; wherein the detector is configured to identify components therein; and wherein a detection signal associated with identified components is related to an elution time in the first eluant stream; collecting the second eluant stream; wherein the second eluant stream is collected in a first collected fraction; wherein a portion of the second eluant stream is diverted and collected in a second collected fraction; wherein the portion of the second eluant stream diverted and collected separately corresponds to a component and elution time identified in the first eluant stream by identified by the detector; and wherein after the second collected fraction is obtained, the second eluant stream is returned to collection in the first collected fraction; thereby providing an edited green tea extract composition with one or more components omitted from the original composition.

Extract Source and Extracts

The disclosed methods of selective deletion chromatography of the present disclosure can be used with a variety of plant, herbal, and botanical source materials such as the leaves, stems, roots, and other components of the plant. The material can be provided dried, semi-dry, or fresh form. Moreover, the disclosed methods of selective deletion chromatography can be further utilized with microbial source materials, including extracts prepared from cells and/or culture media in which cells are grown. The microbes can be any prokaryotic or eukaryotic microbial species, or combinations of species, including bacterial and fungal species that are believed to have a therapeutic or nutraceutical property. In addition, the disclosed methods of selective deletion chromatography can be further utilized with extracts prepared from animal source materials, including invertebrate species such as sponges, mollusks, insects, and arthropods.

In various aspects, a plant used in the preparation of an extract for use with the disclosed selective deletion chromatography methods can be selected from one or more of herbs, medicinal plants, tea, vegetables and/or spices. Examples of plants that are useful in accordance with the present invention are provided in the list shown below. The plant can also be selected from one or more plants comprising anthocyanins, carotenoids, flavonoids, or other components of pharmaceutical or nutraceutical interest. In general, a plant having one or more desired substances for an edible product can be used, e.g., for food, food supplement, medicinal, cosmetic, well-being, nutraceutical or phytotherapeutical applications. Also, any combination of two or more plants can be used.

The extracts can be crude plant extracts, partially purified extracts (e.g., filtered to remove components above or below a specified molecular weight cutoff, subject to fractional crystallization methods, and/or selective solvent or aqueous extraction of plant material), extracts enriched in certain components such as phytochemicals such as alkaloids, glycosides and/or polysaccharides extracted from the plants. In general, the plant extracts are included in the methods to generate compositions comprising the plant extract(s) in which one or more components have been selectively removed per the disclosed methods, which are referred to herein as "botanical compositions." The plant extracts of the system can be combined and provided as a single botanical composition, or each extract can be provided and maintained as a separate botanical composition. Alternatively, two or more of the plant extracts of the system can be combined and provided as a first botanical composition, along with one or more additional plant extracts of the system which are provided and maintained as separate compositions.

Exemplary plant species from which extracts can be prepared and utilized with the disclosed methods of selective deletion chromatography include, but are not limited to: *Abelmoschus* spp., *Abies* spp., *Abroma augusta*, *Acacia* spp., *Acalypha indica*, *Acanthus mollis*, *Acer* spp., *Achillea* spp., *Achyranthes bidentata*, *Acmella oleracea*, *Acorus calamus*, *Actaea* spp., *Actinidia* spp., *Adansonia digitata*, *Adiantum* spp., *Adoxa moschatellina*, *Aegopodium podagraria*, *Aesculus* spp., *Aframomum* spp., *Agathosma* spp., *Agave* spp., *Agrimonia* spp., *Ajuga* spp., *Alaria esculenta*, *Albizia* spp., *Alcea rosea*, *Alchemilla vulgaris*, *Aletris farinosa*, *Alisma* spp., *Alliaria petiolata*, *Allium* spp., *Alnus* spp., *Aloe* spp., *Aloysia citriodora*, *Alpinia* spp., *Althaea officinalis*, *Amaranthus* spp., *Ammivisnaga*, *Amomum villosum*, *Amorphophallus konjac*, *Amyris balsamifera*, *Anacardium occidentale*, *Ananas comosus*, *Andrographis paniculata*, *Anemarrhena asphodeloides*, *Angelica* spp., *Angostura trifoliata*, *Aniba rosaeodora*, *Annona* spp., *Anogeissus latifolia*, *Anredera baselloides*, *Antennaria dioica*, *Anthemis* spp., *Anthriscus* spp., *Anthyllis vulneraria*, *Antirrhinum majus*, *Aphanes arvensis*, *Apium graveolens*, *Arachis hypogaea*, *Aralia* spp., *Arbutus unedo*, *Arctium* spp., *Argania spinosa*, *Armoracia rusticana*, *Artemisia* spp., *Artocarpus altilis*, *Ascophyllum nodosum*, *Asimina triloba*, *Aspalathus linearis*, *Asparagus* spp., *Asplenium* spp., *Astracantha* spp., *Astragalus* spp., *Astrantia major*, *Athamanta macedonica*, *Atractylodes* spp., *Avena* spp., *Averrhoa carambola*, *Baccharis genistelloides*, *Bacopa monnieri*, *Bactris gasipaes*, *Balanites aegyptiaca*, *Ballota* spp., *Bambusa* spp., *Barbarea* spp., *Bellis perennis*, *Berberis* spp., *Bergenia crassifolia*, *Bertholletia excelsa*, *Beta vulgaris*, *Betula* spp., *Bixa orellana*, *Blainvillea acmella*, *Borago officinalis*, *Boronia megastigma*, *Boswellia* spp., *Brassica* spp., *Bupleurum* spp., *Bursera tomentosa*, *Caesalpinia bonduc*, *Cakile maritima*, *Calendula* spp., *Calluna vulgaris*, *Calophyllum inophyllum*, *Camelina* spp., *Canarium acutifolium*, *Canavalia ensiformis*, *Cannabis sativa*, *Capparis spinosa*, *Capsella bursa-pastoris*, *Carex arenaria*, *Carica papaya*, *Carissa carandas*, *Carlina* spp., *Carpinus betulus*, *Carthamus* spp., *Carum carvi*, *Cassia* spp., *Castanea sativa*, *Catalpa bignonioides*, *Ceanothus americanus*, *Cecropia peltata*, *Cedrus libani*, *Ceiba pentandra*, *Centaurea* spp., *Centaurium erythraea*, *Centella asiatica*, *Centranthus ruber*, *Cerasus* spp., *Ceratonia siliqua*, *Cercis siliquastrum*, *Ceterach officinarum*, *Cetraria islandica*, *Chaenomeles speciosa*, *Chamaemelum nobile*, *Chamaecrista noname*, *Chelone glabra*, *Chenopodium* spp., *Chimaphila umbellata*, *Chiococca alba*, *Chionanthus virginicus*, *Chlorella vulgaris*, *Chondrus crispus*, *Chrysanthellum* spp., *Chrysophyllum cainito*, *Chrysopogon zizanioides*, *Cichorium* spp., *Cinchona* spp., *Cinnamomum* spp., *Cistanche salsa*, *Cistus* spp., *Citrullus lanatus*, *Citrus* spp., *Cladonia rangiferina*, *Clematis* spp., *Clinopodium vulgare*, *Clitoria ternatea*, *Cnicus benedictus*, *Cochlearia officinalis*, *Cocos nucifera*, *Codonopsis pilosula*, *Coffea* spp., *Coix lacryma-jobi*, *Cola* spp., *Combretum* spp., *Commiphora* spp., *Conyza canadensis*, *Copaifera langsdorffii*, *Coptis* spp., *Corallina officinalis*, *Cordia myxa*, *Coriandrum sativum*, *Cornus domestica*, *Cornus* spp., *Corrigiola telephiifolia*, *Corylus avellana*, *Corymbia citriodora*, *Coscinium fenestratum*, *Cotinus coggygria*, *Crambe maritima*, *Crataegus* spp., *Crithmum maritimum*, *Crocus sativus*, *Crossostephium chinense*, *Croton nitens*, *Cruciata laevipes*, *Cryptocarya agathophylla*, *Cucumis* spp., *Cucurbita maxima*, *Cuminum cyminum*, *Cupressus sempervirens*, *Curcuma* spp., *Cuscuta* spp., *Cyamopsis tetragonoloba*, *Cyathula officinalis*, *Cyclanthera pedata*, *Cydonia oblonga*, *Cymbopogon* spp., *Cynara* spp., *Cyperus rotundus*, *Cytinus hypocistis*, *Daemonorops draco*, *Dahlia pinnata*, *Daucus carota*, *Dendranthema grandiflorum*, *Descurainia sophia*, *Dianthus caryophyllus*, *Dimocarpus longan*, *Dioscorea* spp., *Diospyros* spp., *Diplotaxis tenuifolia*, *Dipsacus* spp., *Dorstenia contrajerva*, *Dracocephalum moldavica*, *Drimys winteri*, *Drosera* spp., *Dunaliella salina*, *Durio zibethinus*, *IDurvillea antartica*, *Dysphania botrys*, *Echinacea* spp., *Echium plantagineum*, *Elaeis guineensis*, *Elettaria cardamomum*, *Eleutherococcus senticosus*, *Elymus repens*, *Epilobium* spp., *Equisetum* spp., *Erica* spp., *Eriobotrya japonica*, *Eriodictyon californicum*, *Erodium cicutarium*, *Eruca vesicaria*, *Eryngium campestre*, *Eschscholtzia*, *Eucalyptus* spp., *Eucheuma* spp., *Eucommia ulmoides*, *Eugenia uniflora*, *Euphrasia* spp., *Euterpe oleracea*, *Evernia prunastri*, *Exostema caribaeum*, *Fabiana imbricata*, *Fagopyrum esculentum*, *Fagus sylvatica*, *Fallopia* spp., *Ferula assa-foetida*, *Ficus* spp., *Filipendula* spp., *Foeniculum vulgare*, *Forsythia suspensa*, *Fragaria* spp., *Frangula* spp., *Fraxinus* spp., *Fucus* spp., *Fumaria officinalis*, *Galega officinalis*, *Galeopsis segetum*, *Galium* spp., *Garcinia* spp., *Gardenia jasminoides*, *Gastrodia elata*, *Gaultheria procumbens*, *Gelidium* spp., *Gentiana lutea*, *Geranium* spp., *Geum* spp., *Ginkgo biloba*, *Glycine max*, *Glycyrrhiza* spp., *Gossypium herbaceum*, *Gracilaria gracilis*, *Griffonia simplicifolia*, *Grindelia* spp., *Guaiacum* spp., *Guazuma ulmifolia*, *Gynos-* temma pentafillum, Gypsophila paniculata, Haematococcus pluvialis, Haematoxylum campechianum, Hamamelis virginiana, Handroanthus impetiginosus, Haplopappus baylahuen, Harpagophytum spp., Hebanthe eriantha, Hedeoma pulegioides, Hedera helix, Hedychium coronarium, Helianthus spp., Helichrysum spp., Heracleum sphondylium, Herniaria spp., Hesperis matronalis, Hibiscus sabdariffa, Hieracium pilosella, Hierochloe odorata, Himanthalia elongata, Hippophae rhamnoides, Hizikia fusiformis, Hordeum vulgare, Houttuynia cordata, Humulus lupulus, Hydrangea arborescens, Hygrophila auriculata, Hymenaea courbaril, Hypericum perforatum, Hyssopus officinalis, Ilex paraguariensis, Illicium verum, Impatiens balsamina, Indigofera tinctoria, Inula spp., Ipomoea batatas, Isatis tinctoria, Jasminum spp., Jateorhiza palmata, Juglans spp., Jumellea fragrans, Juniperus communis, Justicia spp., Kaempferia galanga, Kavalama urens, Kickxia spuria, Knautia arvensis, Krameria lappacea, Lactuca spp., Lagerstroemia speciosa, Laminaria spp., Lamium album, Larix spp., Laurus nobilis, Lavandula spp., Lawsonia inermis, Ledum palustre, Lens culinaris Medik, Leonurus cardiaca, Lepidium spp., Leptospermum spp., Lespedeza capitata, Leucanthemum vulgare, Levisticum officinale, Lilium brownii, Linaria vulgaris, Lindera aggregata, Linum usitatissimum, Liquidambar styraciflua, Litchi chinensis, Lithothamnion calcareum, Litsea cubeba, Lobaria pulmonaria, Lonicera japonica, Lotus spp., Luma chequen, Lycium spp., Lycopersicon esculentum, Lycopodium clavatum, Lycopus spp., Lysimachia vulgaris, Lythrum salicaria, Macadamia ternifolia, Macrocystis pyrifera, Magnolia spp., Malpighia glabra, Malus spp., Malva sylvestris, Mammea americana, Mangifera indica, Manihot esculenta, Manilkara zapota, Maranta arundinacea, Marchantia polymorpha, Marrubium vulgare, Marsdenia spp., Mastocarpus stellatus, Matricaria chamomilla, Medicago sativa, Melaleuca spp., Melilotus spp., Melissa officinalis, Melittis melissophyllum, Mentha spp., Mentzelia cordifolia, Menyanthes trifoliata, Mesembryanthemum crystallinum, Mespilus germanica, Mikania amara, Mitchella repens, Momordica spp., Monarda spp., Morinda spp., Moringa oleifera, Morus spp., Murraya koenigii Musaxparadisiaca, Myrciaria dubia, Myrica gale, Myristica fragrans, Myroxylon spp., Myrtus communis, Nardostachys jatamansi, Nasturtium officinale, Nelumbo nucifera, Nepeta spp., Nephelium lappaceum, Nigella sativa, Ocimum spp., Oenanthe aquatica, Oenothera biennis, Olea spp., Ononis spp., Onopordon acanthium, Ophioglossum vulgatum, Ophiopogon japonicus, Opopanax chironius, Opuntia ficus-indica, Orchis mascula, Origanum spp., Orthosiphon spp., Oryza sativa, Oxalis acetosella, Pachira spp., Padus avium, Paeonia spp., Palmaria palmata, Panax spp., Panicum miliaceum, Panzerina lanata, Papaver rhoeas, Parietaria officinalis, Parmelia saxatilis, Parthenium hysterophorus, Parthenocissus tricuspidata, Passiflora incarnata, Pastinaca sativa, Paullinia cupana, Pedalium murex, Pelargonium spp., Perilla frutescens, Persea americana, Persicaria spp., Petiveria alliacea, Petroselinum crispum, Peucedanum ostruthium, Peumus boldus, Phaseolus vulgaris, Phellodendron amurense, Phillyrea latifolia, Phlebodium aureum, Phoenix dactylifera, Photinia melanocarpa, Phyla scaberrima, Phyllanthus spp., Phymatolithon calcareum, Physalis spp., Picea abies, Picramnia antidesma, Pimenta spp., Pimpinella spp., Pinus spp., Piper spp., Pistacia spp., Pisum sativum, Plantago spp., Platycodon grandiflorus, Plectranthus barbatus, Pogostemon cablin, Polygala spp., Polygonatum odoratum, Polygonum aviculare, Populus spp., Porphyra umbilicalis, Portulaca oleracea, Potentilla spp., Prangos pabularia, Primula spp., Protium spp., Prunella vulgaris, Prunus spp., Psidium spp., Pterocarpus spp., Pueraria spp., Pulmonaria officinalis, Punica granatum, Pyrola rotundifolia, Pyropia tenera, Pyrus communis, Quercus spp., Quillaja saponaria, Raphanus spp., Raphia farinifera, Rehmannia glutinosa, Rhamnus spp., Rheum spp., Rhodiola crenulata, Rhus spp., Ribes spp., Robinia pseudoacacia, Roccella phycopsis, Rosa spp., Rosmarinus officinalis, Rubia cordifolia, Rubus spp., Rumex spp., Ruscus spp., Sabatia angularis, Saccharina latissima, Saccharum officinarum, Salix spp., Salvia spp., Sambucus spp., Sanguisorba spp., Sanicula elata, Santalum album, Santolina chamaecyparissus, Saponaria officinalis, Saposhnikovia divaricata, Sarcopoterium spinosum, Sargassum fusiforme, Sarracenia purpurea, Satureja spp., Saussurea costus, Schinus molle, Schisandra chinensis, Scorzonera hispanica, Scrophularia ningpoensis, Scutellaria spp., Secale cereale, Sedum spp., Selenicereus grandiflorus, Sempervivum tectorum, Senna spp., Sequoiadendron giganteum, Serenoa repens, Sesamum indicum, Seseli tortuosum, Sideritis syriaca, Sigesbeckia orientalis, Silaum silaus, Silybum marianum, Simarouba amara, Simmondsia chinensis, Siraitia grosvenorii, Sisymbrium officinale, Sium latifolium, Smilax spp., Solanum spp., Solidago virgaurea, Sorbus aucuparia, Sorghum bicolor, Spatholobus suberectus, Spergularia rubra, Spinacia oleracea, Spirulina spp., Stachys officinalis spp., Stellaria media, Stemmacantha carthamoides, Styphnolobium japonicum, Styrax spp., Symplocarpus foetidus, Syring a vulgaris, Syzygium spp., Tagetes spp., Tamarindus indica, Tamarix gallica, Tanacetum spp., Taraxacum officinale, Terminalia spp., Thalictrum flavum, Theobroma cacao, Thlaspi arvense, Thymus spp., Tilia spp., Trachyspermum ammi, Tragopogon porrifolius, Tribulus terrestris, Trichilia catigua, Trichosanthes kirilowii, Tridax procumbens, Trifolium spp., Trigonella spp., Trillium erectum, Triticum spp., Tropaeolum spp., Tsuga Canadensis, Turnera diffusa, Ulmus spp., Ulvalactuca, Uncaria spp., Undaria pinnatifida, Urtica spp., Usnea spp., Vaccinium spp., Valeriana spp., Valerianel lalocusta, Vanilla planifolia, Veratrum viride, Verbascum spp., Verbena officinalis, Veronica spp., Viburnum spp., Vicia spp., Vigna angularis, Viola spp., Viscum album, Vitex spp., Vitis vinifera, Withania somnifera, Xeranthemum annuum, Yucca spp., Zanthoxylum spp., Zea mays, Zingiber officinale, Ziziphus jujube, or combinations of any of the foregoing plants.

In various aspects, a disclosed extract can be prepared from the leaves of *Camellia sinensis* and/or subspecies thereof, such as *Camellia sinensis* var. *assamica*. In a further aspect, a disclosed extract can be prepared from white tea, yellow tea, green tea, oolong, pu-erh tea and/or black tea leaves, i.e., harvested from leaves of *Camellia sinensis* and/or subspecies thereof, such as *Camellia sinensis* var. *assamica*, but are processed differently to attain varying levels of oxidation. In a further aspect, a disclosed extract can be prepared from kukicha (tea twig), i.e., harvested from twigs and stems of *Camellia sinensis* and/or subspecies thereof, such as *Camellia sinensis* var. assamicai.

In various aspects, a disclosed extract can be prepared from the leaves of *Camellia sinensis* and/or subspecies thereof, such as *Camellia sinensis* var. *assamica*, by using hot water or a C1-05 lower alcohol such as ethanol. For example, an extract prepared from the leaves of *Camellia sinensis* and/or subspecies thereof, such as *Camellia sinensis* var. *assamica*, can be accomplished by hot water extraction, the method comprising addition water at about 2- to about 10-fold the weight of the tea material at a temperature of about 50 to about 80° C. for a period of about 0.5 hours to about 12 hours.

*Fucus vesiculosus*, commonly known as bladderwrack, is a type of kelp having a high iodine content, and containing various polysaccharides, such as fucoidans, which have been shown to have anti-thrombotic, anti-coagulant and wound-healing effects (Colliec, S., et al., Thromb. Res. 1991, 64:143-154; O'Leary, R., et al., *Biol. Pharm. Bull.*, 2004, 27:266-270).

Jaborandi is a general term used for various plants from the genus *Pilocarpus*, primarily with respect to the species: *P. jaborandi, P. pennatifolius, P. trachylophus, P. microphyllus* and *P. spicatus*. Extracts from jaborandi leaves have been used for many years as a herbal medicine for the treatment of various diseases and disorders (Lloyd, J. U. *The Gleaner* 1937, volume 46) and have shown some efficacy in treating skin disorders, such as eczema, pruritus, and psoriasis, as well as in darkening the color of hair and in promoting the growth of the hair (see, *King's American Dispensatory*, Felter & Lloyd, 1898, available from Eclectic Medical Publications, Portland, Oreg.). One of the known active constituents of jaborandi is the alkaloid pilocarpine, which is used in the treatment of glaucoma and in ophthalmic settings for promoting constriction of the pupil of the eye. pilocarpine has also been used to treat xerostomia and related oral symptoms in patients with Sjogren's Syndrome (Vivino, F. B., 2001, *Scandinavian Journal of Rheumatology*, 30:1-39) In addition to pilocarpine, jaborandi contains a number of other alkaloids, as well as terpenes and tannic acids.

*Holarrhena antidysynterica* extracts are known in traditional herbal medicine for their ability to treat amoebic dysentery and other gastric disorders, such as diarrhea, indigestion, flatulence and colic (see, for example, Dictionary of Indian Medicinal Plants, Hussain, A., et al., 1992, Central Institute of Medicinal and Aromatic Plants, Lucknow, India). The bark of *Holarrhena antidysynterica* is also known to have an astringent effect. One of the active constituents of *Holarrhena antidysynterica* is thought to be conessine, a steroidal alkaloid that can be isolated from the bark of *Holarrhena antidysynterica* trees. More than thirty alkaloids have been isolated from *Holarrhena antidysynterica*, including conessine, kurchine, kuchicine, holarrhimine, conarrhimine, conaine, conessimine, iso-conessimine, conimine, holacetin, and conkurchin.

In various aspects, a disclosed extract can be prepared from a *Holarrhena* plant species or subspecies, including, but not limited to, *Holarrhena antidysenterica, Holarrhena febrifuga, Holarrhena floribunda* and *Holarrhena pubescens*. In a further aspect, a disclosed extract can be prepared from the bark of the *Holarrhena* plant

*Rauwolfia serpentina* (Indian snakewood) has been used for centuries in Ayurvedic and traditional Indian medicine as a febrifuge, a treatment for snake bites, diarrhea and dysentery, and for the relief of various central nervous system disorders. *Rauwolfia* alkaloids are used in the treatment of hypertension and severe agitation in patients with mental disorders.

In various aspects, a disclosed extract can be prepared from a *Rauwolfia* plant species or subspecies, including, but are not limited to, *Rauwolfia serpentina, Rauwolfia vomitoria, Rauwolfia canescens* and *Rauwolfia tetraphylla*. In a further aspect, a disclosed extract can be prepared from *Rauwolfia serpentina*.

In various aspects, a disclosed extract can be prepared from a *Solanum* plant species or subspecies, including, but are not limited to, *Solanum americanum, Solanum aculeatissimum* (Loveapple), *Solanum capsicastrum, Solanum carolinense* (Horsenettle), *Solanum citrullifolium, Solanum dulcamara* (Woody Nightshade), *Solanum elaeagnifolium, Solanum erianthum* (Tobacco Nightshade), *Solanum heterodoxum, Solanum integrifolium* (Ruffled Red Eggplant), *Solanum laciniatum* (Tasmanian Kangaroo Apple), *Solanum luteum, Solanum melanocerasum* (Sunberry), *Solanum mammosum* (Apple of Sodom), *Solanum melongena* (Eggplant), *Solanum nigrum* (Black Nightshade), *Solanum oleraceum* (Jagueribo), *Solanum physalifolium, Solanum pseudocapsicum* (Jerusalem Cherry), *Solanum quitoense* (Naranjilla), *Solanum rostratum, Solanum sarrachoides, Solanum sisymbrifolium, Solanum sodomaoum* (Apple of Sodom), *Solamum triflorum, Solanum tuberosum* (Potato) and *Solanum xanthocarpum* (Kantikari).

In various aspects, a disclosed extract can be prepared from a *Buxus* plant species or subspecies, including, but are not limited to, *Buxus acuminata, Buxus balearica, Buxus bodineri, Buxus citrifolia, Buxus crassifolia, Buxus cochinchensis, Buxus cubana, Buxus foliosa, Buxus harlandii, Buxus hildebrandtii, Buxus hyrcana, Buxus macrophylla, Buxus macowani, Buxus madagascarica, Buxus megistophylla, Buxus mexicana, Buxus microphylla* (including *Buxus microphylla japonica, Buxus microphylla koreana* and *Buxus microphylla sinica*), *Buxus papillosa, Buxus portoricensis, Buxus pubescens, Buxus revoluta, Buxus riparia, Buxus rotundifolia, Buxus rugulosa, Bixis rupicola, Buxus sinica, Buxus sempervirens* (Box), *Buxus suffructaca* (Dwarf Box), *Buxus vaccinioides, Buxus rivularis, Buxus rolfei* and *Buxus wallichiana*. In a further aspect, a disclosed extract can be prepared from *Buxus balearica, Buxus bodineri, Buxus harlandii, Buxus microphylla* (including *Buxus microphylla japonica, Buxus microphylla koreana* and *Buxus microphylla sinica*), *Buxus riparia, Buxus rugulosa, Buxus sinica, Buxus sempervirens* (Box) and *Buxus wallichiana*.

In various aspects, a disclosed extract can be prepared from a *Pilocarpus* plant species or subspecies, including, but are not limited to, *Pilocarpus cearensis, Pilocarpus jaborandi* (also known as: *Pernambuco jaborandi*), *Pilocarpus microphyllus* (also known as: Maranham jaborandi), *Pilocarpus officinalis, Pilocarpus pauciflorus* (a subspecies of *Pilocarpus spicatus*), *Pilocarpus pennatifolius* (including *Pilocarpus pennatifolius* jaborandi), *Pilocarpus racemosus* (also known as: *Guadeloupe jaborandi*), *Pilocarpus spicatus* (also known as: Aracati jaborandi) and *Pilocarpus trachylophus*. In a further aspect, a disclosed extract can be prepared from *Pilocarpus pennatifolius, Pilocarpus jaborandi* or *Pilocarpus microphyllus*. In a further aspect, a disclosed extract can be prepared from the leaves and fine stems of the *Pilocarpus* plant.

In various aspects, a disclosed extract can be prepared from a seaweed plant species or subspecies, including, but are not limited to, brown seaweed (Phaeophyceae), a red seaweed (Rhodophyceae) or a green seaweed (Chlorophyta). Exemplary brown seaweeds (or kelps) include, but are not limited to *Fucus, Laminara* (for example, *Laminaria digitata, Laminaria saccharina* or *Laminaria japonica*), *Sargassum* (*Sargassum natan* or *Sargassum* fluitan), *Ascophyllum* (for example, *Ascophyllum nodosum*) and *Ecklonia* species. Exemplary red seaweeds include, but are not limited to *Porphyra* and *Chondrus* species, for example, *Chondrus crispus*. Exemplary green seaweeds include, but are not limited to, *Ulva* species, for example, *Ulva latuca*. In a further aspect, a disclosed extract can be prepared from a *Fucus* species or subspecies, including, but are not limited to, *Fucus amylaceus* (Ceylon Moss), *Fucus canaliculatus* (Wrack), *Fucus digitatus, Fucus gardneri, Fucus helminthocorton* (Corsican Moss), *Fucus natans* (Gulf-Weed),

*Fucus nodosus* (Knobbed Wrack), *Fucus serratus* (Black Wrack), *Fucus siliquosus* (Wrack), *Fucus spiralis* and *Fucus vesiculosus* (bladder-wrack).

In various aspects, a disclosed extract can be prepared from *Panax ginseng* (Chinese ginseng, panax, ren shen, jintsam, ninjin, Asiatic ginseng, Japanese ginseng, Oriental ginseng, Korean red ginseng). The extract prepared from this plant source can comprise ginsenosides (protopanaxadiols and protopanaxatriols types), which are believed to have beneficial effects, including immune modulator, anti-inflammatory, antioxidant, and anticancer effects.

In various aspects, a disclosed extract can be prepared from *Rhodiola rosea* (Golden Root, Roseroot). The extract prepared from this plant source can comprise phenylpropanoids (rosavin, rosin, rosarin (specific to *R. rosea*), phenyl-ethanol derivatives (salidroside, rhodioloside, tyrosol), flavanoids (catechins, proanthocyanidins, rodiolin, rodionin, rodiosin, acetylrodalgin, tricin), monoterpenes (rosiridol, rosaridin), triterpenes (daucosterol, beta-sitosterol), and phenolic acids (chlorogenic and hydroxycinnamic, gallic acids). It can further comprise organic acids (gallic, caffeic, and chlorogenic acids) and p-Tyrosol.

The proportion of total plant material used to prepare the extracts for the system of the present disclosure that is derived from a plant is between about 15% and about 95% w/w. In various aspects, the proportion of steroidal alkaloid-containing plant material is between about 20% and about 90% w/w of the total plant material used to prepare the extracts for the system. In another aspect, the proportion of plant material is between about 25% and about 90% w/w of the total plant material used to prepare the extracts used in the disclosed methods of selective deletion chromatography. In a further aspect, the proportion of plant material is between about 30% and about 85% w/w of the total plant material used to prepare the extracts for the system. In a still further aspect of the present disclosure, the proportion of plant material is between about 30% and about 60% w/w of the total plant material used to prepare the extracts for the system. In a yet further aspect of the present disclosure, the proportion of steroidal alkaloid-containing plant material is between about 30% and about 50% w/w of the total plant material used to prepare the extracts for the system.

Plant material is obtained from the selected plants by various standard techniques known to one skilled in the art. The plant material used in the preparation of the extracts can be the entire plant, or it can be one or more distinct parts of the a plant, such as leaves, seeds, roots, stems, flowers, fronds, bark, branches, twigs, or various combinations thereof.

The plant extracts of the present disclosure can be prepared from plant material harvested from unstressed ("natural") plants or from plants that have been treated with one or more stressor prior to harvest. The term "stressor," as used herein, refers to a factor, such as a physical stress, a chemical compound, or a biological agent that is applied to a plant in order to increase the production of certain components, e.g., phytochemicals, prior to harvesting the plant. The stressor can be a chemical stressor and/or a physical stressor. Examples of chemical stressors include, but are not limited to, organic and inorganic acids, fatty acids, glycerides, pitospholipids, glycolipids, organic solvents, amino acids and peptides, monosaccharides, oligosaccharides, polysaccharides and lipopolysaccharides, phenolics, alkaloids, terpenes and terpenoids, antibiotics, detergents, polyamines, peroxides, and ionophores. Examples of physical stressors include, but are not limited to, ultraviolet radiation, low temperature, high temperature, osmotic changes (for example, induced by salt or sugars), and nutritional deprivation (for example, depriving the plant of an essential nutrient, such as nitrogen, phosphorus or potassium).

The extracts can be prepared using fresh plant material or the plant material can be treated, for example, by drying, freezing, lyophilizing, or some combination thereof, prior to preparation of the extracts. The plant material can be used immediately after harvest or it can be stored for a period of time before preparation of the extract. If desired the plant material can undergo one or more of the above treatments prior to storage.

Plant material from one or more of the selected plants can be combined prior to preparation of the extract, or separate extracts can be prepared from each individual plant and either combined at a later stage or maintained as separate extracts. In an aspect of the present disclosure, the plant material from at least two of the selected plants is combined prior to preparing the extract. In a further aspect, the plant material from all the selected plants is combined prior to preparing the extract. In still another aspect, the plant material from the selected plants is not combined prior to preparing the extracts, and the extracts are maintained as separate extracts. In still another aspect, the plant material from the selected plants is not combined prior to preparing the extracts, and the extracts are combined together after preparation.

Plant Extracts

As discussed herein above, the plant material used to prepare the extracts can be fresh, dried or frozen. The extract can be prepared by simply crushing or fragmenting the plant material. For example, the plant material can be pounded, crushed or sliced mechanically, using a grinder, hammer mill, knife mill, tooth mill, blender, pestle and mortar, or other device to fragment the plant parts into small pieces or particles, or the plant material can be frozen in liquid nitrogen and then crushed or fragmented into smaller pieces. Other size reduction methods known in the art can also be used.

Alternatively, the plant extracts can be prepared by contacting the plant material with one or more solvents. If desired, the plant material can be crushed or fragmented as described above prior to being contacted with said solvent(s) in order to present a greater surface area to the solvent. The plant material can be crushed or fragmented under pressure, as appropriate, in order to provide a greater surface area for subsequent solvent contact.

In an aspect of the present disclosure, the plant extract is prepared by contacting the plant material with one or more solvents. In another aspect, the plant material is crushed or fragmented prior to being contacted with the one or more solvents.

When a solvent is used to prepare the extract, the solvent can be an aqueous solvent, an organic solvent, an aqueous-organic mixture, or a mixture of two or more organic solvents. Aqueous solvents suitable for use in the preparation of the extracts include, but are not limited to, water, various aqueous buffers and solutions of organic and/or inorganic salts. The pH of the aqueous solutions can be adjusted to a suitable value by addition of acids and bases as is known in the art and can range from a pH of between about 2 and about 12. Suitable organic solvents include, various natural oils, primary alcohols, such as methyl alcohol (methanol), ethyl alcohol (ethanol), 1-propanol and 1-butanol; secondary alcohols such as 2-propanol and 2-butanol; tertiary alcohols such as 2-methyl-2-propanol; liquid polyhydric alcohols such as glycerine and glycols; and other known organic solvents such as acetone, tetrahydrofuran, acetonitrile, 1,4-dioxane, pyridine, dimethylsulfoxide, N,N-dimethyl formamide, diethyl ether, hexane, heptane, dichloromethane and ethyl acetate, or a combination of the above solvents.

Exemplary oils that can be used as solvent include, but are not limited to, vegetable oils, such as almond, anise, balm, bay, bergamot, borage, cajeput, canola, castor, cedarwood, cinnamon, clove, coconut, corn, cottonseed, evening primrose, flaxseed, grape seed, hempnut, jojoba bean, Karanj (*Pongamia glabra*), lavender, linseed, macadamia, mustard, Neem (*Azadirachta indica*), olive, orignaum (thyme), peanut, rapeseed, safflower, sesame, soybean, sunflower, Tea Tree, walnut and wheat germ oil, or mineral oils, such as liquid paraffin, or a combination of any of the above.

Exemplary glycols include, but are not limited to, ethylene glycol, propylene glycol, diethylene glycol, dipropylene glycol and 1,3-butylene glycol.

In an aspect of the present disclosure, the solvent can comprise an aqueous solvent, a lower alcohol, a natural oil, or a combination thereof. It is understood herein that a "lower alcohol" refers to an alcohol having 1 to 4 carbon atoms, such as a primary, secondary, tertiary or liquid polyhydric alcohol. In a further aspect, the lower alcohol is selected from methyl alcohol (methanol), ethyl alcohol (ethanol), 1-propanol, 1-butanol, 2-propanol, 2-butanol, 2-methyl-1-propanol, 2-methyl-2-propanol, glycerine, ethylene glycol, propylene glycol, diethylene glycol, dipropylene glycol and 1,3-butylene glycol. In a still further aspect, the solvent comprises a vegetable oil.

In various aspects, aqueous-organic mixtures can comprise a ratio of organic solvent(s):aqueous solvent(s) of about 2:1 to 1:20. In a further aspect, the solvent used in the preparation of the extracts can be an aqueous-organic mixture comprising a ratio of organic solvent(s):aqueous solvent(s) of about 1:1 to 1:15. In a still further aspect, the solvent used in the preparation of the extracts can be an aqueous-organic mixture comprising a ratio of organic solvent(s):aqueous solvent(s) of about 1:2 to 1:10.

In various aspects, extraction with a solvent can utilize a supercritical gas, such as carbon dioxide, or by using, for example, ethanol, hexane, acetone, R134a (1,1,1,2-tetrafluoroethane), carbon dioxide and hydrofluorocarbons. In one embodiment, the extraction can be carried out by using at least one solvent at room temperature and under atmospheric pressure. Extraction may also be performed by using a mixture of different solvents. In a further aspect, extraction may be performed using at least one solvent, such as for example R134a or carbon dioxide, at different temperatures and at different pressures and different states (liquid or gaseous). For example, extraction may be performed using solvents in a liquid state (such as solvent that are volatile or non-volatile at room temperature), in a subcritical state (such as water at a temperature above 100° C. and a pressure above 1 bar), or in a supercritical state (such as carbon dioxide at a temperature above 31° C. and a pressure above 73 bar).

Certain plants may require specific extraction conditions (time, temperature, solid/liquid ratio) due to the ingredients contained therein, which may be temperature sensitive or must not be subjected to certain extraction conditions. For example, extraction of lycopene from tomatoes should be performed by using specific enzymes to liberate the product from tomatoes cells. In connection with the present disclosure, processing aids may be used to improve extraction, such as pH modifiers (such as, for example, NaOH or organic acids), microwaves, pressure, ultrasound, enzymes such as for example proteases, amylases, cellulose, and/or pectinases. Whenever reference is made herein to "extraction", the term includes the aforementioned alternative extraction means. The extraction used in connection with the present disclosure can be performed in a continuous or discontinuous matter. The extraction conditions are well known to the skilled artisan and described in standard text books, such as Handbook of Separation Techniques for Chemical Engineers, Third Edition (March 1997), Philip A. Schweitzer, McGraw-Hill Inc.

General Extraction Methods

As a first step in the extraction process, the plant material and solvent(s) are combined and mixed thoroughly. The plant material and solvent(s) are combined in a ratio of between about 10:1 to about 1:100 w/w plant material:solvent(s), in a ratio of between about 5:1 to about 1:70 w/w plant material:solvent(s), in a ratio of between about 3:1 to about 1:60 w/w plant material:solvent(s), in a ratio of between about 1:2 to about 1:50 w/w plant material:solvent(s), in a ratio of between about 1:1 to about 1:50 w/w plant material:solvent(s), in a ratio of between about 1:1 to about 1:30 w/w plant material:solvent(s), or in a ratio of between about 1:1 to about 1:10 w/w plant material:solvent(s), or any ratio within the foregoing ranges. In an alternative aspect of the present disclosure, the amount of plant material employed in the initial extraction step is between about 1% to about 50% w/w.

The overall extraction process can comprise a single extraction step, or it can comprise multiple (i.e., two or more) extraction steps. Typically, each extraction step comprises contacting the plant material with a solvent with adequate mixing over a period of time selected as known in the art, depending on known factors, such as the starting material, the extraction process, the extraction temperature, the ratio of solvent to plait material, and the like.

Various extraction methods known in the art can be employed and may entail, for example, one or more of maceration, remaceration, digestion, agitation, agitation maceration, filtration, vortex extraction, centrifugation, ultrasonic extraction, countercurrent extraction, percolation, repermolation, evacoation (extraction under reduced pressure), diacolation and solid liquid extraction under continuous reflux in a Soxhlet extractor. Percolation may be suitable when preparing extracts on a large-scale.

The plant material is left in contact with the solvent(s) over a period of time sufficient to ensure adequate exposure of the plant material to the solvent(s) such that active components from the plant material are taken up by the solvent(s). Typically this period of time is between about 1 hour and 4 months, although one skilled in the art will appreciate that longer or shorter times may be appropriate. The solvent can be heated prior to contacting the plant material, for example, to a temperature between about 10° C. and about 150° C. prior to being added to the plant material. Alternatively, the plant material can be boiled gently in the solvent for a short period of time and then allowed to cool. The extraction step is can be conducted at a temperature between about 4° C. and about 65° C., between about 10° C. and about 60° C., between about 20° C. and about 60° C., between about 25° C. and about 50° C., or at any temperature within the foregoing ranges. The extraction process can be carried out in a normal atmosphere, or it can be carried out in an inert gas atmosphere when oxidation of the ingredients of the extract is a concern. This may be useful, for example, where the extraction is carried out at temperature above 40° C.

In one aspect of the present disclosure, the extraction procedure is conducted over a period of time between about 1 hour and about 4 months at a temperature between about 4° C. and about 50° C. As indicated above, the solvent can be heated prior to being combined with the plant material for the extraction process. Adequate contact of the plant material with the solvent can be encouraged by shaking or otherwise agitating the suspension either periodically or continuously. In one aspect of the present disclosure, the extraction is carried out in the dark.

The liquid extract is then separated from the solid (insoluble) matter. This separation can be achieved by one or more standard processes known to those skilled in the art, such as filtration (regular, suction, vacuum or under pressure), ultrafiltration, centrifugation, ultracentrifugation, or other means known in the art to separate solids from a solution. If required, the solid material (or marc) thus obtained can be pressed and the resulting liquid added to the extract.

In various aspects, e.g., when further extraction step(s) are to be carried out, the solid material (or mare) can be recovered and submitted to one or more additional extractions as described above, and the extracts combined. The mare can be used "as is" or it can be incinerated or calcined prior to the additional extraction(s). Typically, for calcinations, the pressed marc is spread out in a fireproof dish and steadily heated from below. In general, the temperature for the calcination process is kept below about 400° C., to avoid melting and fusing of the resultant salt. The calcination will usually proceed in stages and pass through different color changes, the first change being the carbonization of the mare, which is black, then through different shades of brown and orange, then finally grey and then white. The salts/ashes obtained from the calcination process can be added back to the initial extract and a subsequent extraction conducted using the initial liquid extract as solvent, or the salts can be added to a new solvent and a further extraction carried out, and the extract obtained added to the initial extract. In one aspect, the salts/ashes obtained from the calcination process comprise an oligomeric form of one or more phytochemicals.

It is also contemplated that additional ingredients may be added to the mixture of the plant material and solvents, for example, to improve the quality of the extract. These additional ingredients may include acids, such as nitric acid. These additional ingredients may be added to either the solvent at the time of first maceration of the plant material, or they may be added to the mixture of the plant material and solvent. The amount of these additional ingredients may vary between 0.1% and 5% of the volume of the solvent added to the plant material. In one aspect of the disclosure, 1% v/v nitric acid is added to the solvent. In another aspect, nitric acid is added to the solvent at the time of first maceration.

In an aspect of the present disclosure, the extracts are prepared by crushing or fragmenting the plant material to provide a pulp, then adding solvent to the pulp in a ratio of about 2:1 to about 1:20 w/w plant material:solvent and mixing thoroughly. The mixture is allowed to stand for between about 1 hour to 100 days in a dark and cool environment. The mixture is shaken frequently to ensure complete extraction of the relevant components from the plant material into the solvent. After the extraction period, the suspension can be left for an additional time of between about 30 minutes to 10 days to allow the larger solid particles to settle at the bottom of the extraction vessel. The solid material is then removed to yield the liquid plant extract.

In an aspect of the present disclosure, the extracts are prepared by crushing or fragmenting the plant material to provide a pulp, then mixing the pulp with an oil in a ratio between about 2:1 to about 1:50 w/w plant material:oil. The temperature of the oil used in this step can be between about 10° C. to about 150° C. Alternatively, the plant material may be simmered gently for between about one minute and 2 hours after being dispersed in the oil. In a specific aspect, the plant material may be simmered gently for between about one and sixty minutes after being dispersed in the oil. In one aspect, the oil/pulp mixture is then mixed with liquid paraffin in a ratio of between 3:1 and 1:3 w/w plant material:liquid paraffin, for example, 2:3 w/w plant material:liquid paraffin, followed by mixing with about 0.2% to 2% w/w of the same or a different oil. The final mixture is allowed to stand for between about 7 to 10 days in dark and cool place with shaking twice daily to ensure complete extraction of the relevant components from the plant material into the oil. After the extraction period, the solid material can be removed if desired, for example, by filtration.

In an aspect of the present disclosure, the extracts are prepared by crushing or fragmenting the plant material to provide a pulp, then mixing with an aqueous solvent in a ratio of between 1:2 to 1:20 w/w. The temperature of the aqueous solvent used in this step can be between about 10° C. to about 150° C. Alternatively, the plant material may be simmered gently for between about one minute and 2 hours after being dispersed in the aqueous solvent. In a specific aspect, the plant material may be simmered gently for between about one and sixty minutes after being dispersed in the aqueous solvent. In one aspect, the aqueous solvent/pulp mixture is then mixed with an organic solvent in a ratio between about 1:1 to about 1:20 w/w plant material:solvent. A second organic solvent can be added at this stage, if desired, in an amount between about 0.2% to about 20% w/w. The mixture is allowed to stand for a time between about 1 hour and 100 days in a dark and cool environment with frequent shaking to ensure complete extraction of the relevant components from the plant material into the solvent. After the extraction period, the suspension can be left for an additional time of between about 30 minutes to 10 days to allow larger solid particles to settle at the bottom of the vessel and, if desired, the solid material can be removed, for example, by filtration.

In an aspect of the disclosure, the extracts are prepared by crushing or fragmenting the plant material to provide a pulp, then mixing with a solvent in a ratio between about 1:2 to about 1:10 w/w. The mixture is then incubated for between about 21 days to 100 days in the dark at about 30° C. to about 40° C. with frequent shaking to ensure complete extraction of the relevant components from the plant material into the solvent. After the extraction period, the suspension can be left for an additional time of between about 30 minutes to 10 days to allow larger solid particles to settle at the bottom of the vessel. If desired, the solid material can then be removed, for example, by filtration.

In various aspects of the present disclosure, the solvent is an organic solvent. In another aspect, the solvent is an aqueous-organic mixture. In a further aspect, the solvent is an aqueous-organic mixture having a ratio of organic solvent:aqueous solvent of about 1:2 to 1:10.

In various aspects of the present disclosure, after the initial extraction, the solid material is removed (for example, by filtration) and subjected to a calcinations process. In another aspect, the calcined solid material is added back to the initial liquid extract and subjected to a further extraction. In a further aspect, the calcined material and initial liquid extract are combined and incubated for between about 21 days and 100 days in the dark at a temperature of about 30°

C. to about 40° C., with frequent shaking. In a still further aspect, about 2% to about 20% propylene glycol is added to the combined calcined material and initial extract prior to the second extraction. The plant extract can then be further incubated without shaking for about 30 minutes to about 30 days to allow any solid material to settle. In one aspect, the plant extract is incubated for 21 days to allow solid material to settle. The solid material can be removed, for example, by filtration, if desired.

The present disclosure also contemplates that other methods known in the art may be employed to prepare the plant extract, for example, the method as generally described in U.S. Patent Application 20040156920.

After the extraction process, extracts may be concentrated, if desired, prior to being used in the disclosed selective deletion chromatography methods by removing some or a substantial portion of the solvent and/or water. The extracts may also be fractionated, using methods common to those of skill in the art (such as a second extraction, filtration, size fractionation by gel filtration or gradient centrifugation, etc.), in order to provide extracts enriched in phytochemicals, such as alkaloids, glycosides and/or polysaccharides and/or submitted to a decolorization process. If desired, the extracts thus prepared may be subjected, for example, to the selective removal of individual unwanted ingredients. In one aspect, the extracts have a final solids content of about 5% to about 10% by weight and are used "as is." In another aspect, the solvent is substantially or completely removed by drying, for example, by spray or freeze drying.

Pharmaceutical Compositions

As noted above, the plant extracts described herein above are utilized in the disclosed methods of selective deletion chromatography and the resulting composition can be used to prepare a pharmaceutical composition of the present disclosure. If the extract has been prepared from one or more plant sources and used in the disclosed selective deletion chromatographic methods, the resulting composition is a termed a plant pharmaceutical composition or botanical pharmaceutical composition. In various aspects, the botanical pharmaceutical composition of the present disclosure consist of a series of chromatographic peaks pooled together in which one or more peaks present in the complete extract have been removed or deleted using the disclosed methods. In a further aspect, the botanical pharmaceutical composition of the present disclosure consist of a series of chromatographic peaks or fractions pooled together in which one or more peaks present in the complete extract have been removed or deleted using the disclosed methods, and in which, the pooled peaks or fractions are further subjected to concentration and/or solvent removal.

The botanical pharmaceutical composition of the present disclosure can be further formulated by various methods known in the art for preparation of pharmaceutical or nutraceutical Botanical pharmaceutical composition (e.g., see "Remington: The Science and Practice of Pharmacy" (formerly "Remington's Pharmaceutical Sciences"); Gennaro, A., Lippincott, Williams & Wilkins, Philadelphia, Pa. (2000).

For example, botanical pharmaceutical composition of the present disclosure can further comprise one or more preservatives and/or anti-oxidants to improve the stability and/or shelf life of the composition. Examples of suitable preservatives aid anti-oxidants include, but are not limited to, propylene glycol, parabens (such as isopropylparaben, isobutylparaben, methylparaben and propylparaben), diazolidinyl urea, essential oils (such as oils from caraway, cinnamon, clove, cumin, eucalyptus, lavender, lemon, rose, rosemary, sage, sandalwood and thyme), grapefruit seed extract and vitamin E oil (such as T-50 vitamin E oil), or combinations thereof.

The present disclosure also contemplates the formulation of the botanical pharmaceutical composition by mixing the extract(s) with a physiologically acceptable carrier. Excipients, binders, diluents, and other additives, such as preservatives, stabilizers, emulsifiers, buffers, coloring agents, fragrances, anti-oxidants, thickening agents, ultra-violet light stabilizers, and the like can also be included in the final composition. Other active ingredients including other plant extracts, moisturizers, vitamins and minerals and the like, can also be added. When the composition comprises more than one extract, the extracts can be formulated together to provide the botanical composition, or the extracts can be formulated independently and the respective formulations subsequently combined using a diluent or the like to provide the final botanical composition. Alternatively, each extract can be formulated independently and maintained as a separate botanical composition. As yet another alternative, the extracts(s) can be formulated independently, followed by mixing of at least two formulations to provide one botanical composition, and the other extract(s) can be maintained as separate botanical pharmaceutical composition.

Thus, in various aspects of the present disclosure, the disclosed botanical pharmaceutical composition comprise two or more extracts that are mixed together followed by the addition of physiological carriers. In a further aspect of the present disclosure, a botanical composition comprises two or more extracts that are formulated individually and then mixed. In still another embodiment, two or more extracts are formulated individually and kept as separate Botanical pharmaceutical composition. In various aspects, the disclosed Botanical pharmaceutical composition prepared by the disclosed selective deletion chromatographic methods comprise at least one botanical composition prepared from a green tea leaves.

The botanical pharmaceutical composition according to the present disclosure may be in solid, semi-solid or liquid form, including both aqueous and non-aqueous liquid forms, and can be provided in unit dosage form where appropriate. The botanical pharmaceutical composition of the present disclosure can be provided in a variety of conventional forms including, but not limited to, solutions, aqueous suspensions, oily suspensions, dispersible powders, dispersible granules, tablets, emulsions, hydrophobic creams, hydrophilic creams, liquid creams, lotions, ointments, waxes, gels, pastes, jellies, tinctures, liniments, sprays, aerosols, sticks, on sponges or cotton applicators, or as solutions or suspensions in an aqueous liquid, a non-aqueous liquid, an oil-in-water emulsion, or a water-in-oil liquid emulsion.

The botanical pharmaceutical composition according to the present disclosure may be in solid, semi-solid or liquid form, including both aqueous and non-aqueous liquid forms, and can be provided in unit dosage form where appropriate. The botanical pharmaceutical composition of the present disclosure can be provided in a variety of conventional forms including, but not limited to, solutions, aqueous suspensions, oily suspensions, dispersible powders, dispersible granules, tablets, emulsions, hydrophobic creams, hydrophilic creams, liquid creams, lotions, ointments, waxes, gels, pastes, jellies, tinctures, liniments, sprays, aerosols, sticks, on sponges or cotton applicators, or as solutions or suspensions in an aqueous liquid, a non-aqueous liquid, an oil-in-water emulsion, or a water-in-oil liquid emulsion.

Botanical pharmaceutical composition formulated as aqueous suspensions contain the extract(s) in admixture with excipients suitable for the manufacture of aqueous suspensions. Such excipients are suspending agents, for example, sodium carboxymethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example hepta-decaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxy-benzoate and/or one or more coloring agents.

Botanical pharmaceutical composition can be formulated as oily suspensions by suspending the extract(s) in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Coloring agents may be added and the formulations may be preserved by the addition of an anti-oxidant such as ascorbic acid.

Dispersible powders and granules suitable for preparation of an aqueous suspension by the addition of water or another carrier provide the extract(s) in admixture with a dispersing or wetting agent, suspending agent and one or more preservatives. Suitable dispersing or wetting agents and suspending agents are exemplified by those described above. Additional excipients, for example, coloring agents, can also be present.

Botanical pharmaceutical composition of the present disclosure can also be in the form of oil-in-water emulsions. The oil phase may be a vegetable oil, for example, olive oil or *arachis* oil, or a mineral oil, for example liquid paraffin, or mixtures of these. Suitable emulsifying agents may be naturally-occurring gums, for example, gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monooleate. The emulsions can also contain coloring agents.

In various aspects of the present disclosure, the botanical pharmaceutical compositions are formulated with one or more carriers selected from the group of: water, glycols, esters, glycerine, oils and alcohols. An exemplary cosmetic carrier known in the art comprises an aqueous alcoholic solution containing ethanol, propanol or isopropanol, together with a lower alkyl($C_1$-$C_4$) glycol, such as ethylene glycol or propylene glycol. A thickener or gelling agent can be added. Dimethicone and other volatile silicone solvents are also useful.

Nutraceutical Compositions

As noted above, the plant extracts described herein above are utilized in the disclosed methods of selective deletion chromatography and the resulting composition can be used to prepare a nutraceutical composition of the present disclosure. If the extract has been prepared from one or more plant sources and used in the disclosed selective deletion chromatographic methods, the resulting composition is a termed a plant nutraceutical composition or botanical nutraceutical composition. In various aspects, the nutraceutical composition of the present disclosure consist of a series of chromatographic peaks pooled together in which one or more peaks present in the complete extract have been removed or deleted using the disclosed methods. In a further aspect, the nutraceutical composition of the present disclosure consist of a series of chromatographic peaks or fractions pooled together in which one or more peaks present in the complete extract have been removed or deleted using the disclosed methods, and in which, the pooled peaks or fractions are further subjected to concentration and/or solvent removal.

Nutraceutically acceptable carriers assist or make possible the formation of a dosage form for a bioactive material and include diluents, binding agents, lubricants, glidants, disintegrants, coloring agents, and flavorants and nutrients. A carrier is nutraceutically acceptable if, in addition to performing its desired function, it is non-toxic, well tolerated upon ingestion, and does not interfere with absorption of bioactive materials. The nutraceutically acceptable carrier can be comprised of one or more binders, excipients, buffers, and flavorants and the flavorants may be selected from calcium carbonate, dextrose, sodium carbonate, magnesium stearate, mannitol, sorbitol, and xylitol. The binders, excipients, buffers, and flavorants and the flavorants can be selected from calcium carbonate, dextrose, sodium carbonate, magnesium stearate, mannitol, sorbitol, and xylitol.

In various aspects, a nutraceutical composition which can be in the form of a solid powder, caplets, tablets, lozenges, pills, capsules, or a liquid, and which may be administered alone or in suitable formulation with other components. For example, the nutraceutical composition of the present invention may be administered in one or more caplets or lozenges as practical for ease of administration. Each of the vitamins and minerals is commercially available, and can be blended to form a single composition or can form multiple compositions, which may be co-administered. More preferably, the composition of the present invention is in the form of a powder form for subsequent reconstitution by addition of a liquid into a beverage for consumption by the patient.

To prepare the nutraceutical compositions of the present disclosure, a composition prepared by the disclosed selective deletion chromatography methods may be formulated as intimate admixture with a suitable nutraceutically acceptable carrier according to conventional compounding techniques. The nutraceutically acceptable carrier may take a wide variety of forms depending upon the form of the preparation desired for administration, e.g., oral administration as, for example but not limited to, drug powders, crystals, granules, small particles (which include particles sized on the order of micrometers, such as microspheres and microcapsules), particles (which include particles sized on the order of millimeters), beads, microbeads, pellets, pills, microtablets, compressed tablets or tablet triturates, molded tablets or tablet triturates, and in capsules, which are either hard or soft and contain the composition as a powder, particle, bead, solution or suspension. The nutraceutical composition can also be sublingual, nasal, topical, or parenteral administration. In various aspects, the nutraceutical composition can be formulated as a controlled release system.

In preparing the nutraceutical composition in a dosage form selected from oral, topical and parenteral, any usual media may be utilized. For liquid preparations (e.g., suspensions, elixirs, and solutions), media containing, for example water, oils, alcohols, flavoring agents, preservatives, coloring agents and the like may be used. Carriers such as starches, sugars, diluents, granulating agents, lubricants, binders, disintegrating agents and the like may be used to prepare oral solids (e.g., powders, caplets, pills, tablets, capsules, and lozenges). Controlled release forms may also be used. Because of their ease in administration, caplets, tablets, pills, and capsules represent the most advantageous oral dosage unit form, in which case solid carriers are employed. If desired, tablets may be sugar coated or enteric coated by standard techniques. All of these pharmaceutical carriers and compositions are well known to those of ordinary skill in the art. See generally, e.g., Wade & Waller, Handbook of Pharmaceutical Excipients (2nd ed. 1994).

In various aspects, the nutraceutical composition can comprise any nutraceutically acceptable excipient, carrier or mixture thereof. As used herein, the term "nutraceutically acceptable excipient or carrier" refers to a non-toxic, inert solid, semi-solid, diluent, encapsulating material or formulation auxiliary of any type. Exemplary excipients include, but are not limited to diluents or fillers, such as dextrates, dicalcium phosphate, calcium sulfate, lactose, cellulose, kaolin, mannitol, sodium chloride, dry starch, sorbitol, sucrose, inositol, powdered sugar, bentonite, microcrystalline cellulose, or hydroxypropylmethylcellulose may be added to the inhibitor molecule to increase the bulk of the composition. Also, binders, such as but not limited to, starch, gelatin, sucrose, glucose, dextrose, molasses, lactose, acacia gum, sodium alginate, extract of Irish moss, panwar gum, ghatti gum, mucilage of isapgol husks, carboxymethylcellulose, methylcellulose, polyvinylpyrrolidone, Veegum and starch arabogalactan, polyethylene glycol, ethylcellulose, and waxes, may be added to the supplement to increase its cohesive qualities. Additionally, lubricants, such as but not limited to, talc, magnesium stearate, calcium stearate, stearic acid, hydrogenated vegetable oils, polyethylene glycol, sodium benzoate, sodium acetate, sodium chloride, leucine, carbowax, sodium lauryl sulfate, and magnesium lauryl sulfate may be added to the supplement. Also, glidants, such as but not limited to, colloidal silicon dioxide or talc may be added to improve the flow characteristics of a powdered supplement. Finally, disintegrants, such as but not limited to, starches, clays, celluloses, algins, gums, crosslinked polymers (e.g., croscarmelose, crospovidone, and sodium starch glycolate), Veegum, methylcellulose, agar, bentonite, cellulose and wood products, natural sponge, cation-exchange resins, alginic acid, guar gum, citrus pulp, carboxymethylcellulose, or sodium lauryl sulfate with starch may also be added to facilitate disintegration of the supplement in the intestine.

In various aspects, the disclosed compositions prepared by the disclosed selective deletion chromatography methods can be formulated to protect the composition from degradation by the acidic conditions of the stomach and from interactions with proteins, such as pepsin, present in the stomach. Such a formulation may include a pH-dependent enteric coating to prevent release until after gastric emptying. Thus, in some aspects, the nutraceutical composition can be enteric coated.

An enteric coated nutraceutical composition can be formulated as enteric coated tablets, beads or granules, which may optionally contain a lubricant such as, but not limited to, magnesium stearate.

The enteric coating may include one or more pH dependent polymers. The pH dependent polymers may remain intact at pH values lower than about 4.0 and dissolve at pH values higher than 4.0, preferably higher than 5.0, most preferably about 6.0. Exemplary pH-dependent polymers include, but are not limited to, methacarylic acid copolymers, methacrylic acid-methyl methacrylate copolymers (e.g., EUDRAGIT® L100 (Type A), EUDRAGIT® S100 (Type B), Rohm GmbH, Germany; methacrylic acid-ethyl acrylate copolymers (e.g., EUDRAGIT® L100-55 (Type C) and EUDRAGIT® L30D-55 copolymer dispersion, Rohm GmbH, Germany); copolymers of methacrylic acid-methyl methacrylate and methyl methacrylate (EUDRAGIT® FS); terpolymers of methacrylic acid, methacrylate, and ethyl acrylate; cellulose acetate phthalates (CAP); hydroxypropyl methylcellulose phthalate (HPMCP) (e.g., HP-55, HP-50, HP-55S, Shinetsu Chemical, Japan); polyvinyl acetate phthalates (PVAP) (e.g., COATERIC®, OPADRY® enteric white OY-P-7171); polyvinylbutyrate acetate; cellulose acetate succinates (CAS); hydroxypropyl methylcellulose acetate succinate (HPMCAS), e.g., HPMCAS LF Grade, MF Grade, HF Grade, including AQOAT® LF and AQOAT® MF (Shin-Etsu Chemical, Japan); Shinetsu Chemical, Japan); shellac (e.g., MARCOAT™ 125 & MARCOAT™ 125N); vinyl acetate-maleic anhydride copolymer; styrene-maleic monoester copolymer; carboxymethyl ethylcellulose (CMEC, Freund Corporation, Japan); cellulose acetate phthalates (CAP) (e.g., AQUATERIC®); cellulose acetate trimellitates (CAT); and mixtures of two or more thereof at weight ratios between about 2:1 to about 5:1, such as, for instance, a mixture of EUDRAGIT® L 100-55 and EUDRAGIT® S 100 at a weight ratio of about 3:1 to about 2:1, or a mixture of EUDRAGIT® L 30 D-55 and EUDRAGIT® FS at a weight ratio of about 3:1 to about 5:1.

The pH dependent polymers can be incorporated in an amount from about 10% to 90%, preferably from about 20% to 80% and most preferably from about 30% to 70% by weight of the dosage unit or supplement. The polymer(s) can be incorporated into the formulation either prior to or after granulation or they can be added into the supplement either as a dry material, or they can be dispersed or dissolved in an appropriate solvent, and dispersed during granulation.

An enteric coated nutraceutical composition can include enteric coated beads in a capsule, enteric coated microspheres in a capsule, enteric coated microspheres provided in a suspension or mixed with food, which are particularly convenient for pediatric administration, and enteric coated compressed tablets. The capsule can be a hard-shell gelatin capsule or a cellulose capsule. In particular, the composition or herbal supplement may be formulated as an enteric coated capsule. In certain embodiments, an herbal supplement comprising an anti-spasmodic composition, such as peppermint oil is administered in a tablet form that is backfilled with microcrystalline cellulose. Alternatively, the peppermint oil may be administered without the use of an enteric coating.

In some aspects, the nutraceutical composition can be directly compressed, with or without any excipients, into a tablet or other herbal supplement having a nutraceutically acceptable hardness and friability. Preferably, the directly compressible herbal supplement can be compressed into tablets having a hardness of greater than 4 kp (kiloponds), preferably a hardness of 8 to 14 kp, more preferably a hardness of 10 to 13 kp. A directly compressible composition can be compressed into a tablet that has a friability of not more than 1% loss in weight, preferably less than 0.8% loss in weight, more preferably less than 0 5% loss in weight.

The administration of the nutraceutical composition will typically be administered over several weeks in a manner, which provides an effective amount of each of the desired nutrients so as to ensure that the demand for the nutrients by the induced mitochondrial energy production or stimulated ATP production, is satisfied.

The nutraceutical composition may be formulated in a unit dose form. Such unit dose will generally comprise an amount in the range of from about 0.01 µg to about 15,000 mg, about 0.1 µg to about 1000 mg, and about 0.1 µg to about 500 mg of the composition. The nutraceutical composition may be taken in doses, one to six times a day in a manner such that the total daily dose for a 70 kg adult will generally be in the range of from about 0.1 µg to 40,000 mg, about 1 µg to 10,000 mg, or about 0.5 µg to 20,000 mg. The daily dose of the nutraceutical composition can be about 0.1 µg mg/kg/day to about 50 mg/kg/day body weight, about 0.5 µg mg/kg/day to about 40 mg/kg/day, or about 1.0 µg mg/kg/day to about 20 mg/kg/day are effective in one or several administrations per day in order to obtain the desired results. The administered dose depends on the age, state of health, and weight of the recipient, the extent of various enzymatic activities in the recipient, the type of additional treatments that may be carried out at the same time, and the type of desired effect. During the course of the treatment, the concentration of the nutraceutical compositions may be monitored to ensure that the desired level is maintained.

The nutraceutical composition may be administered in the form of daily doses such as in liquid, tablet, capsule or pill form. Alternatively, the nutraceutical composition may be administered via one or more dosage forms each comprising varying amounts of at least one of water-soluble and fat-soluble energy nutrients over a period of time.

Kits

In various aspects, the present disclosure pertains to kits comprising a disclosed composition, a disclosed pharmaceutical composition, or a disclosed nutraceutical composition; and one or more of: (a) at least one agent known to cause an inflammatory response; (b) at least one agent known to cause a dysfunction in the innate immunity system; (c) at least one agent known to cause a dysfunction in TNFα expression; (d) at least one agent known to treat an inflammatory response; (e) at least one agent known to treat a dysfunction in the innate immunity system; (f) at least one agent known to treat a dysfunction in TNFα expression; (g) instructions for treating an inflammatory response; (h) instructions for treating a dysfunction in the innate immunity system; or (i) instructions for treating to case a dysfunction in TN Fa expression.

The present disclosure additionally contemplates that the above-described system can be provided in kit form. The kit comprises the extracts or composition(s) disclosed herein in a suitable container or containers. The present disclosure contemplates that the extracts or compositions of the system call be provided in a ready to use format or, alternatively, in lyophilized form and the kit can further comprise reagents suitable for the reconstitution of the lyophilized extracts. The present disclosure further contemplates that the extracts can be provided as solutions and the kit can contain additional components to be added to the extracts to facilitate their application to affected areas. Where appropriate, the kit may also contain mixing vessels and other instruments or containers that facilitate the reconstitution or mixing of components of the kit.

The kit can further provide an appropriate usage regimen over a prescribed period of time for the system, for example in the form of a set of instructions, generally written instructions. The kit may further comprise one or more of the plant extracts that make up the system in a substantially diluted form suitable for oral administration, for example, as a homeopathic preparation or herbal tincture. Alternatively, where appropriate, the kit may further comprise one or more of the plant extracts of the system in tablet form for oral administration. There may also be associated with the kit a notice in the form prescribed by a governmental agency regulating the manufacture, use or sale of biological products, which notice reflects approval by the agency of manufacture, use or sale for human or animal administration.

Effective Dose

A response to a prophylatic and/or treatment method of the disclosure can, for example, also be measured by determining the physiological effects of the treatment or medication, such as the decrease or lack of disease symptoms following administration of the treatment or pharmacological agent. Other assays will be known to one of ordinary skill in the art and can be employed for measuring the level of the response. For example, physical and biochemical diagnostic methods are available in the medical arts to ascertain the likelihood that a subject has an inflammatory disorder, e.g., a disorder associated with abnormal levels of reactive oxygen species or TNFα, and to determine the putative stage of the disease can be used to ascertain the level of response to a prophylactic and/or treatment method of the disclosure. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount can depend upon the degree to which an individual has abnormal levels and/or activity of a secretase pathway associated protein or secretase pathway associated protein complex.

The factors involved in determining an effective amount are well known to those of ordinary skill in the art and can be addressed with no more than routine experimentation. It is generally preferred that a maximum dose of the pharmacological agents of the disclosure (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

The therapeutically effective amount of a pharmacological composition of the disclosure is that amount effective to modulate an inflammatory disorder, e.g., a disorder associated with abnormal levels of reactive oxygen species or TNFα, and/or the level or activity of an inflammatory disorder-associated protein or other bioactive molecule, e.g., a protein or other bioactive molecule involved in a signaling or cytokine pathway, and reduce, prevent, or eliminate the symptoms of the inflammatory disorder. For example, testing can be performed to determine the level and/or activity of a secretase pathway associated protein or secretase pathway associated protein complex in a subject's tissue and/or cells. Additional tests useful for monitoring the onset, progression, and/or remission, of inflammatory disorders such as those described above herein, are well known to those of ordinary skill in the art. As would be understood by one of ordinary skill, for some disorders (e.g., an inflammatory disorder) an effective amount would be the amount of a pharmacological composition of the disclosure that decreases the level and/or activity of a an inflammatory disorder-associated protein or other bioactive molecule, e.g., a protein or other bioactive molecule involved in a signaling or cytokine pathway, to a level and/or activity that diminishes the disorder, as determined by the aforementioned tests.

In the case of treating a particular disease or condition the desired response is inhibiting the progression of the disease or condition. This may involve only slowing the progression of the disease temporarily, although more preferably, it involves halting the progression of the disease permanently. This can be monitored by routine diagnostic methods known to one of ordinary skill in the art for any particular disease. The desired response to treatment of the disease or condition also can be delaying the onset or even preventing the onset of the disease or condition.

Research Tools

Since compositions of the present disclosure possess anti-inflammatory activity, e.g., modulation of ROS and/or TNFα levels, such compositions are also useful as research tools. Accordingly, one aspect of the disclosure relates to a method of using a composition of the disclosure as a research tool, the method comprising conducting a biological assay using a composition of the disclosure. Compositions of the disclosure can also be used to evaluate new chemical compounds. Thus another aspect of the disclosure relates to a method of evaluating a test compound in a biological assay, comprising: (a) conducting a biological assay with a test compound to provide a first assay value; (b) conducting the biological assay with a composition of the disclosure to provide a second assay value; wherein step (a) is conducted either before, after or concurrently with step (b); and (c) comparing the first assay value from step (a) with the second assay value from step (b). Exemplary biological assays include a cell-based ROS production assays and expression of TNFα in a mammal. Still another aspect of the disclosure relates to a method of studying a biological system or sample comprising a cell capable of producing TNFα in response to an inflammatory stimulus or a suitable animal model of inflammatory disease, the method comprising: (a) contacting the cell or animal model with a composition of the disclosure; and (b) determining the effects caused by the composition on the cell or animal model.

Before proceeding to the Examples, it is to be understood that this disclosure is not limited to particular aspects described, and as such may, of course, vary. Other systems, methods, features, and advantages of foam compositions and components thereof will be or become apparent to one with skill in the art upon examination of the following drawings and detailed description. It is intended that all such additional systems, methods, features, and advantages be included within this description, be within the scope of the present disclosure, and be protected by the accompanying claims. It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

REFERENCES

Anderson, R. A. and Polansky, M. M. J. Agric. Food Chem. (2002) 50(24):7182.

Assuncao, M. and Andrade J. P. Front Biosci. (2015) 20:247-262.

Bao, G. H., Xu J., Hu, F. L., Wan, X. C., Deng, S. X., and Barasch, J. Biometals (2013) 26(6):1041-1050.

Bickford, P. C., Kaneko, Y., Grimmig, B., Pappas, C., Small, B., Sanberg, C. D., Sanberg, P. R., Tan, J., and Shytle, D. R. Age (Dordr). (2015) 37:103.

Boehm, K., Borrelli, F., Ernst, E., Habacher, G., Hung, S. K., Milazzo, S., and Horneber, M. Cochrane Database of Systematic Reviews (2009) Issue 3. Art. No.: CD005004 (doi: 10.1002/14651858.0D005004.pub2).

Braud, L., Peyre, L., de Sousa, G., Armand, M., Rahmani, R., and Maixent, J.-M. Molecules (2015) 20:14985-15002

Chacko, S. M., Thambi, P. T., Kuttan, R., and Nishigak, I. Chin. Med. (2010) 5:13-21.

Colon, M. and Nerin, C. Eur. Food Res. Technol. (2016) 242:211-220.

Crespy, V. and Williamson, G. J. Nutr. (2004) 134:3431S-3440S.

Dajas, F. J. Ethnopharmacol. (2012) 143:383-396.

Deka. A. and Vita, J. A. Pharmacol. Res. (2011) 64:136-145.

Del Rio, D., Stewart, A. J., Mullen, W., Burns, J., Lean, M. E., Brighenti, F., and Crozier, A. J. Agric. Food Chem. (2004) 52(10):2807-2815.

Dulloo, A. G., Seydoux, J., Girardier, L. Chantre, P., and Vandermander, J. Int. J. Obesity. (2000) 24:252-258.

Flowers, A., Lee, J. Y., Acosta, S., Hudson, C., Small, B., Sanberg, C. D., and Bickford, P. C. J. Neuroinflammation. (2015) 12:174.

Forbes, S. C., Holroyd-Leduc, J. M., Poulin, M. J., and Hogan, D. B. Can. Geriatr. J. (2015) 18: 231-245.

Friedman, M., Levin, C., Choi, S.-h., Kozukue, E., and Kozukue, N. J. Food Sci. (2006) 71(6):C328-C337.

Hsieh, T. C. and Wu, J. M. Anticancer Res. (2009) 29:4025-4032.

Hügel, H. M. Adv. Exp. Med. Biol. (2015) 863:95-116.

Ikeda, I., Kobayashi, M., Hamada, T., Tsuda, K., Imaizumi, K., Nozawa, A., Sugimoto, A., and Kakuda, T. J. Agric. Food Chem. (2003) 51(25):7303-7307.

Jakobek, L. Food Chem. (2015) 175:556-567.

Kanakis, C. D., Hasni, I., Bourassa, P., Hamdani, S., Tarantilis, P. A., and Tajmir-Riahi, H. A. Food Chem. (2011) 127:1046-1055.

Khan, N. and Mukhtar, H. Life Sci. (2007) 81:519-533

Kobalka, A., Keck, R. W., and Jankun, J. Cent. Eur. J. Immunol. (2014) 40:1-4.

Lambert, J. D. and Elias, R. J. Arch. Biochem. Biophys. (2010) 501:65-72.

Mandel, S. A., Avramovich-Tirosh, Y., Reznichenko, L., Zheng, H., Weinreb, O., Amit, T., and Youdim. M. B. Neurosignals. (2005) 14:46-60.

Martin, M. D., Calcul, L., Smith, C., Jinwal, U. K., Fontaine, S. N., Darling, A., Seeley, K., Wojtas, L., Narayan, M., Gestwicki, J. E., Smith, G. R., Reitz, A. B., Baker, B. J., and Dickey, C. A. ACS Chem. Biol. (2015) 10:1099-1109.

Molino, S., Dossena, M., Buonocore, D., Ferrari, F., Venturini, L., Ricevuti, G., and Verri, M. Life Sci. (2016) 161:69-77.

Niedzwiecki, A., Roomi, M. W., Kalinovsky, T., and Rath, M. Nutrients. (2016) 8:552-569.

Ozdal, T., Capanoglu, E., and Altay, F. Food Res. Int. (2013) 51:954-970.

Pandareesha, M. D., Mythria, R. B., and Srinivas Bharatha, M. M. Neurochem. Int. (2015) 89:198-208.

Peluso, I., Raguzzini, A., and Serafini, M. Mol. Nutr. Food Res. (2013) 57:784-801.

Peter, B., Boszej, S., and Horvath, R. Eur. Biophys. J. (2017) 46:1-24.

Da Silva Pinto, M. Food Res. Int. (2013) 53:558-567.

Rawel, H. M., Czajka, D., Rohn, S., and Kroll, J. Int. J. Biol. Macromol. (2002) 30:137-150.

Reygaert, W. C. Front. Microbiol. (2014) 5:434.

Sang, S., Lambert, J. D., Ho, C. T., and Yang, C. S. Pharmacol. Res. (2011) 64:87-99.

Schaffer, S., Asseburg, H., Kuntz, S., Muller, W. E., and Eckert, G. P. Mol. Neurobiol. (2012) 46:161-178.

Serafini, M., Del Rio, D., Yao, D. N., Bettuzzi, S., and Peluso, I. Chapter 12: Health benefits of tea. In *Herbal Medicine: Biomolecular, and Clinical Aspects,* 2nd ed.; Benzie, I. F. F., Wachtel-Galor, S., Eds.; CRC Press: Boca Raton, Fla., USA, (2011) pp. 239-262.

Siow, C. M. R. and Mann, G. E. Mol. Aspects Med. (2010) 31:468-477.

Suzuki, T., Pervin, M., Goto, S., Isemura, M., and Nakamura, Y. (2016) 21:E1305.

Szulińska, M., Stępień, M., Kręgielska-Narożna, M., Suliburska, J., Skrypnik, D., Bąk-Sosnowska, M., Kujawska-Łuczak, M., Grzymisławska, M., and Bogdański, P. Food Nutr. Res. (2017) 61:1295525.

Tang, S. N., Singh, C., Nall, D., Meeker, D., Shankar, S., and Srivastava, R. K. J. Mol. Signal. (2010) 5:14.

Thielecke, F. and Boschmann, M. Phytochem. (2009) 70: 11-24.

Valcic, S., Timmermann, B. N., Alberts, D. S., Wächter, G. A., Krutzsch, M., Wymer, J., and Guillén, J. M. Anticancer Drugs. (1996) 7:461-468.

van der Hooft, J. J. J., Akermi, M., Unlu, F. Y., Mihaleva, V., Roldan, V. G., Bino, R. J., de Vos, R. C. H., and Vervoort, J. J. Agric. Food Chem. (2012) 60:8841-8850.

Williams, S. N., Pickwell, G. V., and Quattrochi, L. C. J. Agric. Food Chem. (2003) 51(22)6627-34.

Yang, C. S., Lambert, J. D., Ju, J., Lu, G., and Sang, S. Toxicol Appl Pharmacol. (2007) 224:265-273.

Yang C S, Wang H, Li G X, Yang Z, Guan F, Jin H. Cancer prevention by tea: Evidence from laboratory studies. Pharmacol Res. 2011; 64: 113-122.

Yarmolinsky J, Gon G, Edwards P. Effect of tea on blood pressure for secondary prevention of cardiovascular disease: a systematic review and meta-analysis of randomized controlled trials. Nutr Rev. 2015; 73: 236-246.

EXAMPLES

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Green Tea (*Camellia sinensis*) Extract Preparation.

Green tea (*Camellia sinensis*) for the studies described herein was obtained from Starwest Botanicals, Inc. (Sacramento, Calif.). Briefly, a 400 g lot was distributed equally among 10 filter bags (T-sac), then treated with boiling deionized water (700 mL) in a crystallizing dish for 10 min. After extraction the plant material was removed, the boiling water extract was cooled and filtered. The resulting solution was frozen overnight and lyophilized over a period of 3 days. The procedure provided approximately 8 g of freeze-dried green tea boiling water extract.

LC/MS Profiling.

Chromatographic profiling was conducted with an Agilent 6120 B LC/ESIMS 1200 series preparative LC system (Agilent Technologies, Santa Clara, Calif.). The LC/MS data were analyzed using MassHunter software (Agilent Technologies). Target compounds were identified by the comparison of their mass data and retention times with those previous green tea studies reported in the literature (Anderson, R. A. and Polansky, M. M. J. Agric. Food Chem. (2002) 50(24):7182; Williams, S. N., Pickwell, G. V., and Quattrochi, L. C. J. Agric. Food Chem. (2003) 51(22):6627-34; Del Rio, D., Stewart, A. J., Mullen, W., Burns, J., Lean, M. E., Brighenti, F., and Crozier, A. J. Agric. Food Chem. (2004) 52(10):2807-2815; Friedman, M., Levin, C., Choi, S.-h., Kozukue, E., and Kozukue, N. J. Food Sci. (2006) 71(6): C328-C337; and Ikeda, I., Kobayashi, M., Hamada, T., Tsuda, K., Imaizumi, K., Nozawa, A., Sugimoto, A., and Kakuda, T. J. Agric. Food Chem. (2003) 51(25):7303-7307). Commercially available analytical standards were also used for confirmatory purposes (Sigma-Aldrich Co. LLC, St. Louis, Mo. and Fluka, now Honeywell Research Chemicals, Inc., Morris Plains, N.J.).

Biological Activity Assays.

ROS Measurement. BE(2)-M17 cells were grown in 96-well plates with high glucose DMEM+10% FBS with 4 mM iron sulfate and treated for 48 hours with 10 µg/mL aqueous extracts and/or fractions. ROS levels were measured following a 20 min incubation with 25 µM 2', 7'-dichlorofluorescein diacetate.

TNFα Measurement. BV2 mouse immortalized microglial cells were grown in 75 $cm^2$ flasks with DMEM plus 10% FBS, then plated into 96-well plates with $10^4$ BV2 cells per well. After incubation for 24 hours, the cells were pretreated with 100 µg/ml of aqueous extracts for 24 hours or PBS as control, followed by LPS challenge 100 ng/ml for 12 hours. LPS alone was used as a positive control. Culture media were collected and TNFα in the cell culture media were detected by TNFα ELISA kit (R&D Systems, Inc., Minneapolis, Minn.) according to the manufacturer's protocol.

Exemplary Selective Deletion Chromatography.

Figure 3:
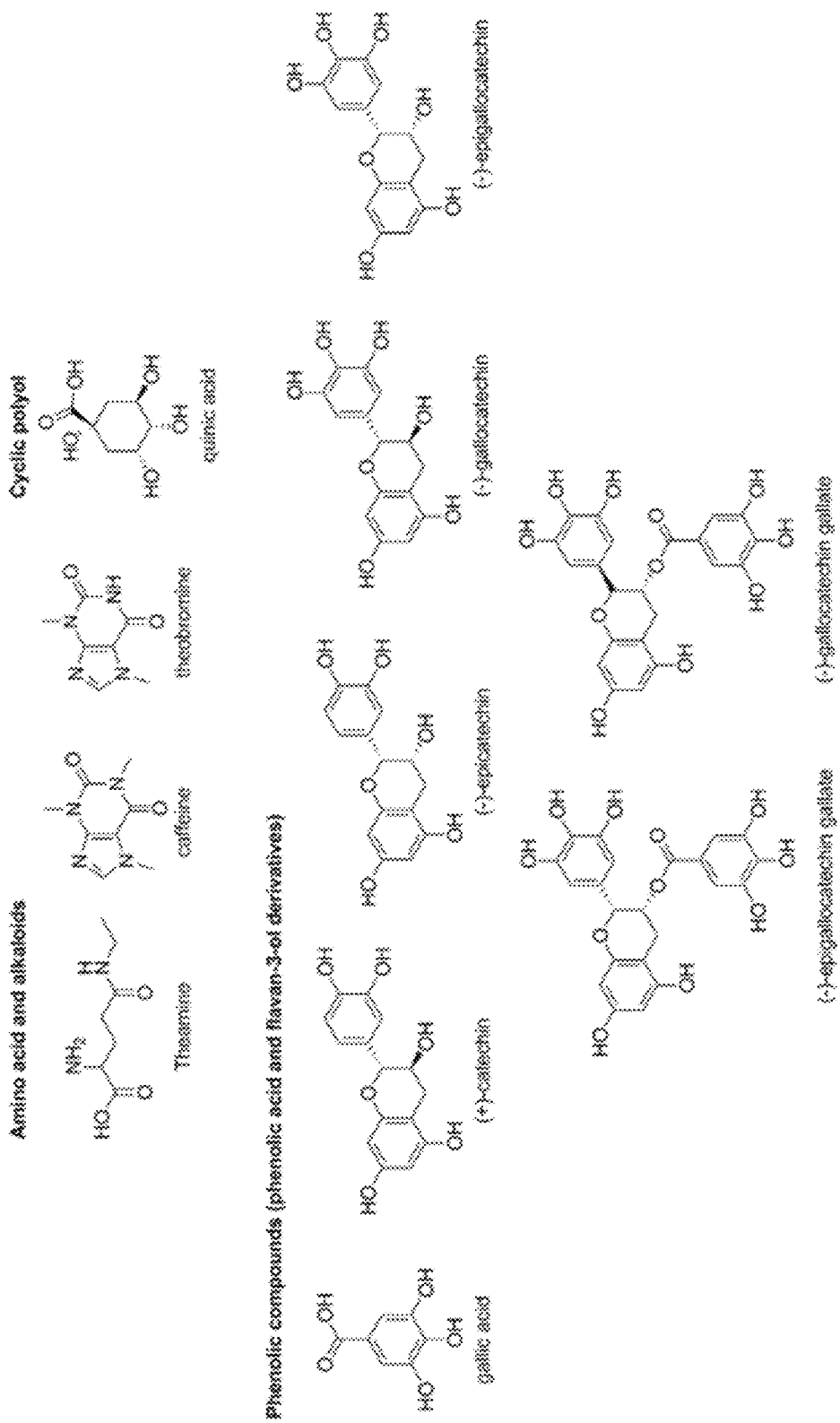
FIG. 3 shows representative chemical structures of compounds that can be present in a green tea extract.

Green tea extract was separated via 10 consecutive injections (75 mg per injection). A representative chromatogram is provided in FIG. 1. Each injection was programed to divert based on time to a collection vessel while the remainder of the sample flowed to a separate vial. In this manner, fractions designated P1 through P9 were generated, as well as a green tea extract devoid of each fraction (designated as fractions GT-1 through GT-9). Representative data regarding the chemical composition of the separated fractions is provided in Table 1 and FIG. 3.

TABLE 1

| Peak | RT$^a$ | m/z$^b$ | Identification | Extract |
|---|---|---|---|---|
| P1 | 3 | 175.1/*, */168.9, */191,1 | theanine, gallic acid, quinic acid | GT-3 |
| P2 | 9 | 181.1/* | theobromine | GT-9 |
| P3 | 10 | 307.1/305.1 | (−)-gallocatechin [GC] | GT-10 |
| P4 | 20 | 307.1/305.1 | (−)-epigallocatechin [EG] | GT-20 |
| P5 | 23-26 | 195/*, 291.1/289.1 | caffeine (minor (+)- catechin) | GT-(23-26) |
| P6 | 30 | 291.1/289.1 | (−)- epicatechin [EC] | GT6 |
| P7 | 32 | 459.1/457.1 | (−)-epigallocatechin-3-gallate [EGCG] | GT-32 |
| P8 | 35 | 459.1/457.1 | (−)-gallocatechin-3-gallate [GCG] | GT-35 |
| P9 | 40 | 443.0/441.1 | (−)-epicatechin-3-gallate [ECG] | GT-40 |

$^a$ minutes;
$^b$ (ESI$^+$/ESI$^-$);
*Not determined.

Exemplary Activity of Selective Deletion Chromatography Fractions

Figure 2:
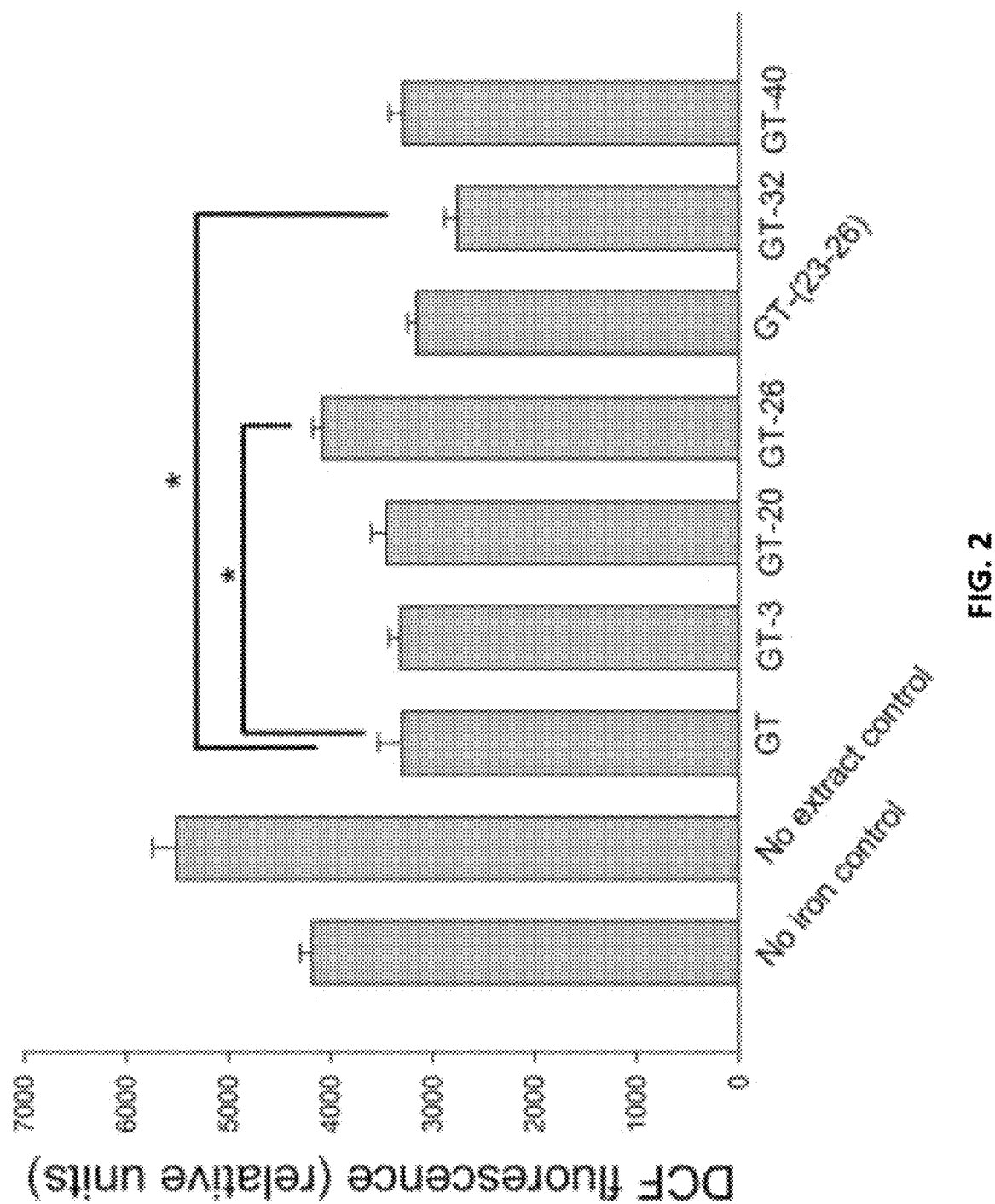
FIG. 2 shows representative data for the effect of mixtures prepared according to the disclosed methods on the production of reactive oxygen species ("ROS"). The data show ROS levels in response to the indicated fractions. ROS was determined as described herein below. The data were analyzed using one-way ANOVA followed post hoc tests. * indicates $p<0.05$ when compared to a complete crude green tea extract.

The biological activity, with regard to production of reactive oxygen species ("ROS"), of representative fractions prepared as described above are compared to a crude green tea extract (referred to hereinafter as "GT") was determined. The data are given in FIG. 2 and demonstrate that the disclosed methods can provide compositions with modulated or refined activated. As shown in FIG. 2, the crude green tea extract shows modest activity in reducing reactive oxygen species (ROS) from challenged neuroblastoma. However, after caffeine, or alternatively, a minor component, (+)-catechin, is removed, (denoted by −26, the retention time (in minutes) where caffeine/catechin eluted), and the 'subtracted extract' (designated "GT-26") is re-analyzed, it was found that there was a significant (p<0.05) increase in ROS occurs compared to the GT sample. Without wishing to be bound by a particular theory, these data suggest that caffeine and/or catechin play a significant role in green tea's ability to reduce ROS to challenged neuroblastoma. In contrast, when (−)-epigallocatechin-3-gallate (EGCG, retention time 32 minutes) was removed, the subtracted extract (designated "GT-32") ability to reduce ROS decreases, suggesting that EGCG interferes with GT's capacity to reduce ROS. The data show that the disclosed 'subtraction chromatography' methods (alternatively referred to as selective deletion chromatography) provide a powerful approach to modulating and refining the activity of extract materials by creating compositions with chemical compositions not otherwise available in a crude or naturally occurring extract mixture. Moreover, the disclosed methods provide tools to deconvolute the relative contributions of components to crude extract bioactivity. In various aspects, the disclosed methods can further comprise automated diversion of fractions based upon mass characteristics instead of based upon the detector response.

Figure 4:
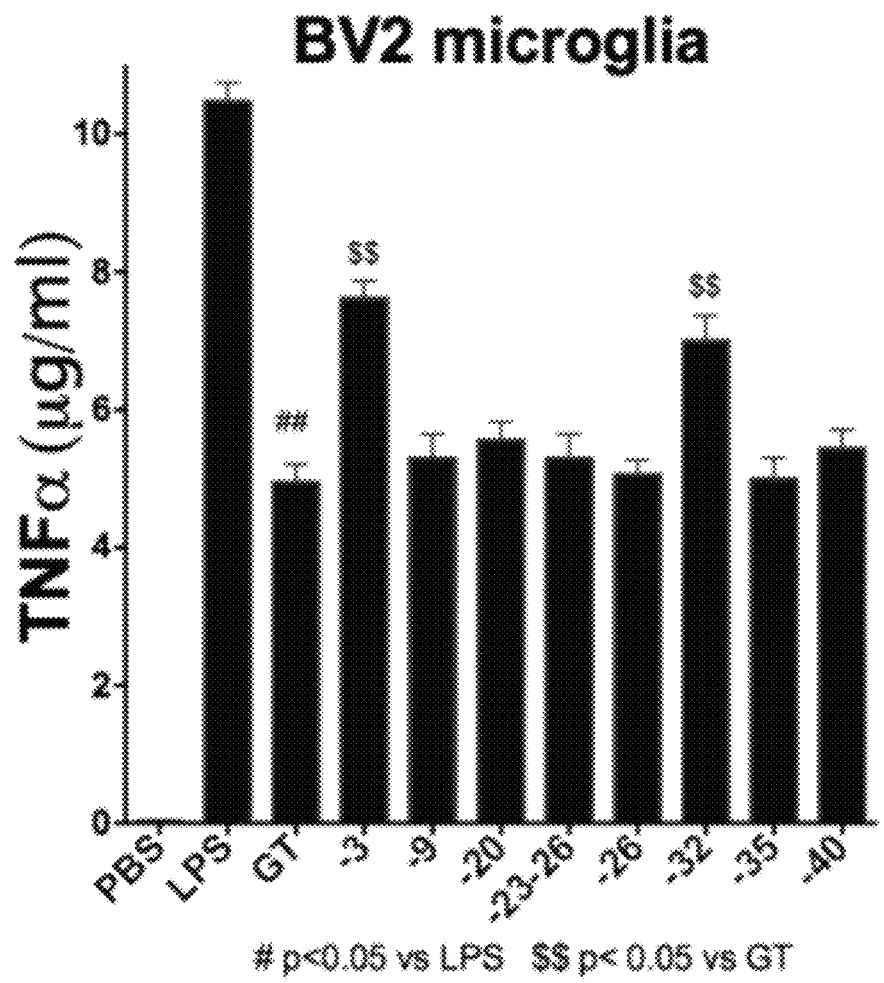
FIG. 4 shows representative data for the effect of mixtures prepared according to the disclosed methods on the production of TNFα. The data show TNFα levels in response to the indicated fractions. TNFα was determined as described herein below. The data were analyzed using one-way ANOVA followed post hoc tests. * indicates $p<0.05$ when compared to a complete crude green tea extract.

BE(2)-M 17 cells were incubated with iron as well as green tea (*Camellia sinensis*) (GT) extracts separated chromatographically and then recombined with all components except the individual components eluted at 3 minutes (GT-3), 20 minutes (GT-20), 26 minutes (GT-26), 23 through 26 minutes (GT-(23-26)), 32 minutes (GT-32), and 40 minutes (GT-40). Reactive oxygen species (ROS) levels were then measured. As shown in FIG. 4, GT-3, GT-20, GT-(23-26), and GT-40 addition did not alter ROS levels. But administering GT-26 increased ROS levels indicating that the component removed contains compounds that decrease ROS. Using standards, we determined that caffeine and catechin were present in this 26 minute peak. We also found that removing the component eluting at 32 minutes (GT-32) decreased ROS levels, so there is a pro-oxidant in this fraction. Epigallochatechin-3-gallate (EGCG) was identified in this peak and accordingly, it has in some cases been shown to have pro-oxidant properties, especially in transformed cells (Braicu, et al., 2013). EGCG is known to stimulate the reduction of iron from $Fe^{3+}$ to $Fe^{2+}$ to activate the Fenton reaction to produce hydroxyl radical [1]. In part due to this property, EGCG is being tested in clinical trials for the treatment of cancer [2]. As proof of concept, we showed that we can use LC/MS to identify components that either increase or decrease the effect of the GT extract on cellular ROS levels in neuroblastoma cells. The data protection from iron-induced ROS, higher antioxidant-like activity was observed with EGCG removed edited mxiture (suggesting it is pro-oxidant) and lower antioxidant activity occurred with caffeine and catechin removed. The use of disclosed methods provides a powerful tool for characterizing interplay of diverse components in a complex crude mixture that result in seemingly contradictory actions of the green tea extract with anti-inflammatory and some antioxidant effects and some pro-oxidant effects.

The effect of the edited extracts on decreasing LPS-induced TNFα secretion in isolated microglia, and the data are shown in FIG. 4. Treatment with GT-3 and GT-32 extracts showed higher TNFα secretion than other SDC extracts. Without wishing to be bound by a particular theory, it is believed that fraction 3 with theamine, gallic acid, quinic acid and other compounds may be important for a substantial portion of the total anti-inflammatory activity of GT, as does the fraction at 32 minutes that is primarily EGCG. It is contemplated in the present disclosure that both fractions 3 and 32 could be removed in a single edited mixture. It is anticipated that removal of both peaks may have additive effects suggesting actions, suggesting action of these peaks via different mechanisms.

It should be emphasized that the above-described aspects of the present disclosure are merely possible examples of implementations set forth for a clear understanding of the principles of the disclosure. Many variations and modifications may be made to the above-described aspect(s) without departing substantially from the spirit and principles of the disclosure. All such modifications and variations are intended to be included herein within the scope of this disclosure and protected by the following claims.

That which is claimed is:

1. A method of preparing a therapeutic or nutraceutical composition for human or animal administration, the therapeutic or nutraceutical composition comprising an edited extract composition prepared from an original composition, the method comprising:

applying an extract sample from the original composition to a liquid chromatography system comprising a chromatography column;

applying a mobile phase to the chromatography column after the extract sample is applied to the chromatography column;

dividing a total eluant volume into a first eluant stream and a second eluant stream, wherein the first eluant stream comprises a minority fraction by volume of the total eluant volume, and wherein the second eluant stream comprises a majority fraction by volume of the total eluant volume;

directing the first eluant stream to a detector configured to identify components therein, wherein a detection signal associated with identified components is related to an elution time in the first eluant stream;

collecting the second eluant stream, wherein the second eluant stream is collected in a first collected fraction for a first given length of time, wherein the second eluant stream is diverted and collected in a second collected fraction for a second given length of time subsequent to the first given length of time, wherein the second given length of time corresponds to a component and elution time identified in the first eluant stream by the detector, and wherein after the second collected fraction is obtained, the second eluant stream is returned to collection in the first collected fraction for a third given length of time, thereby providing the edited extract composition with one or more components omitted from the original composition; and formulating the therapeutic or nutraceutical composition for human or animal administration comprising the edited extract composition.

2. The method of claim 1, wherein the extract sample is obtained from a plant material.

3. The method of claim 2, wherein the plant source is green tea leaves.

4. The method of claim 1, wherein the chromatography column is a reverse phase column.

5. The method of claim 4, wherein the reverse phase column is a C18 column.

6. The method of claim 1, wherein the mobile phase comprises acetonitrile and water.

7. The method of claim 1, wherein the detector is a spectrophotometer.

8. The method of claim 7, wherein the spectrophotometer is capable of detection of substances that absorb in the UV and/or visible wavelength spectrum.

9. The method of claim 1, wherein the detector is a mass spectrometer.

10. The method of claim 9, wherein the mass spectrometer is configured to detect ion peaks of components in the first eluant stream; and wherein detection signal associated with the ion peaks are each related to an elution time.

11. The method of claim 1, wherein the second eluant stream is diverted and collected in a third collected fraction for a fourth length of time.

12. The method of claim 1, wherein the second eluant stream is diverted and collected in a third collected fraction for a fourth given length of time subsequent to the third given length of time, wherein the fourth given length of time corresponds to a component and elution time identified in the first eluant stream by the detector, wherein after the third collected fraction is obtained, the second eluant stream is returned to collection in the first collected fraction for a fifth given length of time.

13. The method of claim 12, wherein the mobile phase comprises:
   7% (v/v) acetonitrile in water at time 0-10 minutes following application of the extract sample to the chromatography column;
   7-15% (v/v) gradient of acetonitrile in water at time 10-30 minutes following application of the extract sample to the chromatography column;
   15-20% (v/v) gradient of acetonitrile in water at time 30-35 minutes following application of the extract sample to the chromatography column; and
   7% (v/v) acetonitrile in water at time 35 minutes and longer following application of the extract sample to the chromatography column.

14. The method of claim 13, wherein the column is 10 mm×250 mm; wherein the particle size of the stationary phase is 5 µm; and wherein the sample comprises about 50-100 mg of green tea extract.

15. The method of claim 14, wherein the detector is a spectrophotometer capable of detection of substances that absorb in the UV and/or visible wavelength spectrum.

16. The method of claim 1, wherein the therapeutic or nutraceutical composition is a nutraceutical composition.

17. The method of claim 14, wherein the detector is a mass spectrometer.

18. The method of claim 1, wherein the second eluant stream is diverted and collected in an addition collected fraction for an additional given length of time that does not overlap with the first, second, or third given lengths of time, the method further comprising adding the additional collected fraction to an extract material to provide an addition-enhanced plant extract.

19. The method of claim 1, further comprising adding an additive to the first collected fraction to provide an addition-edited mixture prior to formulating the dosage form, wherein the dosage form is formulated to comprise the addition-edited mixture.

20. An edited extract composition prepared by the method of claim 1.

* * * * *